US012805836B2

(12) United States Patent
Zhang et al.

(10) Patent No.: US 12,805,836 B2
(45) Date of Patent: Nov. 24, 2026

(54) SYSTEMS AND METHODS FOR REAL-TIME TRACKING OF A TARGET TISSUE USING IMAGING BEFORE AND DURING THERAPY DELIVERY

(71) Applicant: Otsuka Medical Devices Co., Ltd., Tokyo (JP)

(72) Inventors: Jimin Zhang, Bellevue, WA (US); Shayin Jing, Seattle, WA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 0 days.

(21) Appl. No.: 18/937,003

(22) Filed: Nov. 4, 2024

(65) Prior Publication Data

US 2025/0057506 A1 Feb. 20, 2025

Related U.S. Application Data

(60) Continuation of application No. 17/171,940, filed on Feb. 9, 2021, now Pat. No. 12,133,765, which is a
(Continued)

(51) Int. Cl.
*A61B 8/00* (2006.01)
*A61B 8/06* (2006.01)
(Continued)

(52) U.S. Cl.
CPC .............. *A61B 8/4254* (2013.01); *A61B 8/08* (2013.01); *A61B 8/085* (2013.01); *A61B 8/4263* (2013.01);
(Continued)

(58) Field of Classification Search
CPC ......... A61B 8/4254; A61B 8/08; A61B 8/085; A61B 8/4263; A61B 8/5207;
(Continued)

(56) References Cited

U.S. PATENT DOCUMENTS

| | | | |
|---|---|---|---|
| 385,256 | A | 6/1888 | Eggers |
| 3,274,437 | A | 9/1966 | Mastrup |

(Continued)

FOREIGN PATENT DOCUMENTS

| | | |
|---|---|---|
| EP | 0225120 | 6/1987 |
| EP | 0420758 | 4/1991 |

(Continued)

OTHER PUBLICATIONS

Accornero, Neri et al., "Selective Activation of Peripheral Nerve Fibre Groups of Different Diameter by Triangular Shaped Stimulus Pulses", J. Physiol. (1977), 273, _ 539-560, 22 Q9S.

(Continued)

*Primary Examiner* — Baisakhi Roy
(74) *Attorney, Agent, or Firm* — Theresa Ann Raymer

(57) ABSTRACT

Described herein are systems and methods for tracking a target tissue during therapy delivery. A system for identifying an anatomical structure and tracking the motion of the anatomical structure using imaging before and during delivery of a therapy to a patient includes an imaging module and a therapy module. In some cases, the imaging module is configured to identify a region of the anatomical structure in an image, and the therapy module is configured to deliver the therapy to a target tissue. A method for imaging during delivery of a therapy includes acquiring an image, identifying a region of an anatomical structure, tracking the region of the anatomical structure, integrating the tracking, generating a unique template library, determining if a pre-existing template matches the results or if the results should be updated as a new template, and delivering the therapy to the target tissue.

22 Claims, 13 Drawing Sheets

Related U.S. Application Data division of application No. 14/929,056, filed on Oct. 30, 2015, now Pat. No. 10,925,579.

(60) Provisional application No. 62/075,487, filed on Nov. 5, 2014.

(51) Int. Cl.

| | |
|---|---|
| ***A61B 8/08*** | (2006.01) |
| ***A61B 17/00*** | (2006.01) |
| ***A61B 17/225*** | (2006.01) |
| ***A61B 18/00*** | (2006.01) |
| ***A61N 7/02*** | (2006.01) |
| ***G06T 7/246*** | (2017.01) |
| ***G06T 7/44*** | (2017.01) |
| *A61B 18/20* | (2006.01) |
| *A61B 34/20* | (2016.01) |
| *A61B 90/00* | (2016.01) |
| *A61N 5/10* | (2006.01) |
| *A61N 7/00* | (2006.01) |

(52) U.S. Cl.

CPC .......... *A61B 8/5207* (2013.01); *A61B 8/5223* (2013.01); *A61B 17/2256* (2013.01); *A61N 7/02* (2013.01); *G06T 7/246* (2017.01); *G06T 7/248* (2017.01); *G06T 7/44* (2017.01); *A61B 8/06* (2013.01); *A61B 8/4488* (2013.01); *A61B 8/488* (2013.01); *A61B 2017/00699* (2013.01); *A61B 2017/00703* (2013.01); *A61B 2018/00511* (2013.01); *A61B 18/20* (2013.01); *A61B 2034/2051* (2016.02); *A61B 2034/2065* (2016.02); *A61B 2090/378* (2016.02); *A61N 2005/1058* (2013.01); *A61N 2007/003* (2013.01); *A61N 2007/0052* (2013.01); *A61N 2007/0091* (2013.01); *A61N 2007/0095* (2013.01); *G06T 2207/30084* (2013.01)

(58) Field of Classification Search

CPC ..... A61B 8/5223; A61B 17/2256; A61B 8/06; A61B 8/4488; A61B 8/488; A61B 18/20; A61B 2017/00699; A61B 2017/00703; A61B 2018/00511; A61B 2034/2051; A61B 2034/2065; A61B 2090/378; A61B 2034/2055; G06T 7/246; G06T 7/248; G06T 7/44; G06T 2207/30084

See application file for complete search history.

(56) References Cited

U.S. PATENT DOCUMENTS

| | | | |
|---|---|---|---|
| 3,499,437 | A | 3/1970 | Balamuth et al. |
| 3,552,382 | A | 1/1971 | Mount |
| 3,599,477 | A | 8/1971 | Cohen et al. |
| 3,847,016 | A | 11/1974 | Ziedonis |
| 3,927,662 | A | 12/1975 | Ziedonis |
| 3,969,578 | A | 7/1976 | Mezrich et al. |
| 4,059,098 | A | 11/1977 | Murdock |
| 4,167,180 | A | 9/1979 | Kossoff |
| 4,197,856 | A | 4/1980 | Northrop |
| 4,206,763 | A | 6/1980 | Pedersen |
| 4,237,901 | A | 12/1980 | Taenzer |
| 4,273,127 | A | 6/1981 | Auth et al. |
| 4,469,099 | A | 9/1984 | McEwen |
| 4,479,494 | A | 10/1984 | McEwen |
| 4,484,569 | A | 11/1984 | Driller et al. |
| 4,545,386 | A | 10/1985 | Hetz et al. |
| 4,554,925 | A | 11/1985 | Young |
| 4,601,296 | A | 7/1986 | Yerushalmi |
| 4,605,010 | A | 8/1986 | McEwen |
| 4,643,186 | A | 2/1987 | Rosen |
| 4,650,466 | A | 3/1987 | Luther |
| 4,688,578 | A | 8/1987 | Takano et al. |
| 4,702,732 | A | 10/1987 | Powers et al. |
| 4,708,836 | A | 11/1987 | Gain et al. |
| 4,709,698 | A | 12/1987 | Johnston et al. |
| 4,748,985 | A | 6/1988 | Nagasaki |
| 4,757,820 | A | 7/1988 | Itoh |
| 4,770,175 | A | 9/1988 | McEwen |
| 4,773,865 | A | 9/1988 | Baldwin |
| 4,773,899 | A | 9/1988 | Spears |
| 4,784,148 | A | 11/1988 | Dow et al. |
| 4,841,977 | A | 6/1989 | Griffith et al. |
| 4,841,979 | A | 6/1989 | Dow et al. |
| 4,850,363 | A | 7/1989 | Yanagawa |
| 4,858,613 | A | 8/1989 | Fry et al. |
| 4,905,672 | A | 3/1990 | Schwarze et al. |
| 4,913,155 | A | 4/1990 | Dow et al. |
| 4,929,246 | A | 5/1990 | Sinofsky |
| 4,931,047 | A | 6/1990 | Broadwin et al. |
| 4,938,216 | A | 7/1990 | Lele |
| 4,938,217 | A | 7/1990 | Lele |
| 4,955,377 | A | 9/1990 | Lennox et al. |
| 4,957,099 | A | 9/1990 | Hassler |
| 4,957,481 | A | 9/1990 | Gatenby |
| 4,983,169 | A | 1/1991 | Furukawa |
| 5,000,185 | A | 3/1991 | Yock |
| 5,005,579 | A | 4/1991 | Wurster et al. |
| RE33,590 | E | 5/1991 | Dory |
| 5,026,387 | A | 6/1991 | Thomas |
| 5,036,855 | A | 8/1991 | Fry et al. |
| 5,039,774 | A | 8/1991 | Shikinami et al. |
| 5,042,486 | A | 8/1991 | Pfeiler et al. |
| 5,048,527 | A | 9/1991 | Okazaki |
| 5,065,742 | A | 11/1991 | Belikan et al. |
| 5,080,101 | A | 1/1992 | Dory |
| 5,080,102 | A | 1/1992 | Dory |
| 5,093,570 | A | 3/1992 | Dorfi et al. |
| 5,114,423 | A | 5/1992 | Kasprzyk |
| 5,150,712 | A | 9/1992 | Dory |
| 5,170,790 | A | 12/1992 | Lacoste et al. |
| 5,178,135 | A | 1/1993 | Uchiyama et al. |
| 5,178,148 | A | 1/1993 | Lacoste et al. |
| 5,181,522 | A | 1/1993 | McEwen |
| 5,193,527 | A | 3/1993 | Schafer |
| 5,194,291 | A | 3/1993 | D'Aoust et al. |
| 5,211,160 | A | 5/1993 | Talish et al. |
| 5,215,680 | A | 6/1993 | D'arrigo |
| 5,219,401 | A | 6/1993 | Cathignol et al. |
| 5,230,334 | A | 7/1993 | Klopotek |
| 5,230,921 | A | 7/1993 | Waltonen et al. |
| 5,233,994 | A | 8/1993 | Shmulewitz |
| 5,243,988 | A | 9/1993 | Sieben et al. |
| 5,254,087 | A | 10/1993 | McEwen |
| 5,263,957 | A | 11/1993 | Davison |
| 5,290,278 | A | 3/1994 | Anderson |
| 5,311,869 | A | 5/1994 | Okazaki |
| 5,312,431 | A | 5/1994 | McEwen |
| 5,352,195 | A | 10/1994 | McEwen |
| 5,364,389 | A | 11/1994 | Anderson |
| 5,368,591 | A | 11/1994 | Lennox |
| 5,383,896 | A | 1/1995 | Gershony et al. |
| 5,391,140 | A | 2/1995 | Schaetzle et al. |
| 5,391,197 | A | 2/1995 | Burdette et al. |
| 5,394,875 | A | 3/1995 | Lewis et al. |
| 5,394,877 | A | 3/1995 | Orr et al. |
| 5,413,550 | A | 5/1995 | Castel |
| 5,415,657 | A | 5/1995 | Taymor-Luria |
| 5,423,811 | A | 6/1995 | Imran et al. |
| 5,439,477 | A | 8/1995 | McEwen |
| 5,445,608 | A | 8/1995 | Chen et al. |
| 5,453,576 | A | 9/1995 | Krivitski |
| 5,454,373 | A | 10/1995 | Koger et al. |
| 5,454,831 | A | 10/1995 | McEwen |
| 5,471,988 | A | 12/1995 | Fujio et al. |
| 5,474,071 | A | 12/1995 | Chapelon et al. |
| 5,479,375 | A | 12/1995 | Gualtieri |
| 5,492,126 | A | 2/1996 | Hennige et al. |
| 5,501,655 | A | 3/1996 | Rolt et al. |
| 5,503,152 | A | 4/1996 | Oakley et al. |

(56) References Cited

U.S. PATENT DOCUMENTS

| | | | |
|---|---|---|---|
| 5,507,744 | A | 4/1996 | Tay et al. |
| 5,507,790 | A | 4/1996 | Weiss |
| 5,515,853 | A | 5/1996 | Smith et al. |
| 5,520,188 | A | 5/1996 | Hennige et al. |
| 5,522,878 | A | 6/1996 | Montecalvo et al. |
| 5,524,620 | A | 6/1996 | Rosenschein |
| 5,526,815 | A | 6/1996 | Granz et al. |
| 5,534,232 | A | 7/1996 | Denes et al. |
| 5,536,489 | A | 7/1996 | Lohrmann et al. |
| 5,553,618 | A | 9/1996 | Suzuki et al. |
| 5,556,415 | A | 9/1996 | McEwen et al. |
| 5,558,092 | A | 9/1996 | Unger et al. |
| 5,558,672 | A | 9/1996 | Edwards et al. |
| 5,573,497 | A | 11/1996 | Chapelon |
| 5,574,212 | A | 11/1996 | Madsen et al. |
| 5,575,788 | A | 11/1996 | Baker et al. |
| 5,578,055 | A | 11/1996 | McEwen |
| 5,584,853 | A | 12/1996 | McEwen |
| 5,598,845 | A | 2/1997 | Chandraratna |
| 5,601,526 | A | 2/1997 | Chapelon et al. |
| 5,607,447 | A | 3/1997 | McEwen et al. |
| 5,609,485 | A | 3/1997 | Bergman et al. |
| 5,626,601 | A | 5/1997 | Gershony et al. |
| 5,630,837 | A | 5/1997 | Crowley |
| 5,638,823 | A | 6/1997 | Akay et al. |
| 5,643,179 | A | 7/1997 | Fujimoto |
| 5,649,954 | A | 7/1997 | McEwen |
| 5,655,538 | A | 8/1997 | Lorraine et al. |
| 5,657,755 | A | 8/1997 | Desai |
| 5,657,760 | A | 8/1997 | Ying et al. |
| 5,665,073 | A | 9/1997 | Bulow et al. |
| 5,666,954 | A | 9/1997 | Chapelon et al. |
| 5,681,339 | A | 10/1997 | McEwen et al. |
| 5,685,307 | A | 11/1997 | Holland et al. |
| 5,685,839 | A | 11/1997 | Edwards et al. |
| 5,688,266 | A | 11/1997 | Edwards et al. |
| 5,695,493 | A | 12/1997 | Nakajima et al. |
| 5,697,897 | A | 12/1997 | Buchholtz et al. |
| D389,574 | S | 1/1998 | Emerson et al. |
| 5,711,058 | A | 1/1998 | Frey |
| 5,716,374 | A | 2/1998 | Francese et al. |
| 5,720,286 | A | 2/1998 | Chapelon et al. |
| 5,720,287 | A | 2/1998 | Chapelon et al. |
| 5,722,411 | A | 3/1998 | Suzuki et al. |
| 5,726,066 | A | 3/1998 | Choi |
| 5,735,796 | A | 4/1998 | Granz et al. |
| 5,738,635 | A | 4/1998 | Chapelon et al. |
| 5,741,295 | A | 4/1998 | McEwen |
| 5,755,228 | A | 5/1998 | Wilson et al. |
| 5,762,066 | A | 6/1998 | Law et al. |
| 5,769,790 | A | 6/1998 | Watkins et al. |
| 5,788,636 | A | 8/1998 | Curley |
| 5,800,482 | A | 9/1998 | Pomeranz et al. |
| 5,807,285 | A | 9/1998 | Vaitekunas et al. |
| 5,810,007 | A | 9/1998 | Holupka et al. |
| 5,810,810 | A | 9/1998 | Tay et al. |
| 5,817,021 | A | 10/1998 | Reichenberger |
| 5,823,962 | A | 10/1998 | Schaetzle et al. |
| 5,824,015 | A | 10/1998 | Sawyer |
| 5,824,277 | A | 10/1998 | Campos et al. |
| 5,827,204 | A | 10/1998 | Grandia et al. |
| 5,827,268 | A | 10/1998 | Laufer |
| 5,833,647 | A | 11/1998 | Edwards |
| 5,840,028 | A | 11/1998 | Chubachi et al. |
| 5,846,517 | A | 12/1998 | Unger |
| 5,852,860 | A | 12/1998 | Lorraine et al. |
| 5,853,752 | A | 12/1998 | Unger et al. |
| 5,855,589 | A | 1/1999 | McEwen et al. |
| 5,873,828 | A | 2/1999 | Fujio et al. |
| 5,873,845 | A | 2/1999 | Cline et al. |
| 5,879,314 | A | 3/1999 | Peterson et al. |
| 5,882,302 | A | 3/1999 | Driscoll, Jr. et al. |
| 5,882,328 | A | 3/1999 | Levy et al. |
| 5,895,356 | A | 4/1999 | Andrus et al. |
| 5,904,659 | A | 5/1999 | Duarte et al. |
| 5,906,580 | A | 5/1999 | Kline-Schoder et al. |
| 5,911,735 | A | 6/1999 | McEwen et al. |
| 5,919,139 | A | 7/1999 | Lin |
| 5,921,994 | A | 7/1999 | Andreas et al. |
| 5,922,945 | A | 7/1999 | Allmaras et al. |
| 5,931,786 | A | 8/1999 | Whitmore, III et al. |
| 5,931,853 | A | 8/1999 | McEwen et al. |
| 5,935,144 | A | 8/1999 | Estabrook |
| 5,935,146 | A | 8/1999 | McEwen et al. |
| 5,935,339 | A | 8/1999 | Henderson et al. |
| 5,938,600 | A | 8/1999 | Van Vaals et al. |
| 5,951,476 | A | 9/1999 | Beach |
| 5,957,849 | A | 9/1999 | Munro |
| 5,964,782 | A | 10/1999 | Lafontaine et al. |
| 5,976,092 | A | 11/1999 | Chinn |
| 5,979,453 | A | 11/1999 | Savage et al. |
| 5,993,389 | A | 11/1999 | Driscoll, Jr. et al. |
| 5,997,481 | A | 12/1999 | Adams et al. |
| 6,007,499 | A | 12/1999 | Martin et al. |
| 6,014,473 | A | 1/2000 | Hossack et al. |
| 6,033,506 | A | 3/2000 | Klett |
| 6,036,650 | A | 3/2000 | Wu et al. |
| 6,037,032 | A | 3/2000 | Klett et al. |
| 6,039,694 | A | 3/2000 | Larson et al. |
| 6,050,943 | A | 4/2000 | Slayton et al. |
| 6,066,134 | A | 5/2000 | Eggers et al. |
| 6,067,371 | A | 5/2000 | Gouge et al. |
| 6,068,596 | A | 5/2000 | Weth et al. |
| 6,071,239 | A | 6/2000 | Cribbs et al. |
| 6,071,277 | A | 6/2000 | Farley et al. |
| 6,078,831 | A | 6/2000 | Belef et al. |
| 6,083,159 | A | 7/2000 | Driscoll, Jr. et al. |
| 6,087,761 | A | 7/2000 | Lorraine et al. |
| 6,097,985 | A | 8/2000 | Kasevich et al. |
| 6,102,860 | A | 8/2000 | Mooney |
| 6,106,463 | A | 8/2000 | Wilk |
| 6,117,101 | A | 9/2000 | Diederich et al. |
| 6,120,453 | A | 9/2000 | Sharp |
| 6,128,522 | A | 10/2000 | Acker et al. |
| 6,179,831 | B1 | 1/2001 | Bliweis |
| 6,182,341 | B1 | 2/2001 | Talbot et al. |
| 6,200,539 | B1 | 3/2001 | Sherman et al. |
| 6,206,843 | B1 | 3/2001 | Iger et al. |
| 6,213,939 | B1 | 4/2001 | McEwen |
| 6,217,530 | B1 | 4/2001 | Martin et al. |
| 6,221,015 | B1 | 4/2001 | Yock |
| 6,231,507 | B1 | 5/2001 | Zikorus et al. |
| 6,233,477 | B1 | 5/2001 | Chia et al. |
| 6,246,156 | B1 | 6/2001 | Takeuchi et al. |
| 6,254,598 | B1 | 7/2001 | Edwards |
| 6,254,601 | B1 | 7/2001 | Burbank et al. |
| 6,259,945 | B1 | 7/2001 | Epstein et al. |
| 6,263,551 | B1 | 7/2001 | Lorraine et al. |
| 6,267,734 | B1 | 7/2001 | Ishibashi et al. |
| 6,270,458 | B1 | 8/2001 | Barnea |
| 6,277,077 | B1 | 8/2001 | Brisken et al. |
| 6,283,989 | B1 | 9/2001 | Laufer et al. |
| 6,292,695 | B1 | 9/2001 | Webster |
| 6,296,619 | B1 | 10/2001 | Brisken et al. |
| 6,315,441 | B2 | 11/2001 | King |
| 6,315,724 | B1 | 11/2001 | Berman et al. |
| 6,332,089 | B1 | 12/2001 | Acker et al. |
| 6,361,496 | B1 | 3/2002 | Zikorus et al. |
| 6,361,548 | B1 | 3/2002 | McEwen |
| 6,383,151 | B1 | 5/2002 | Diederich et al. |
| 6,399,149 | B1 | 6/2002 | Klett et al. |
| 6,406,759 | B1 | 6/2002 | Roth |
| 6,409,720 | B1 | 6/2002 | Hissong et al. |
| 6,419,669 | B1 | 7/2002 | Frazier et al. |
| 6,425,867 | B1 | 7/2002 | Vaezy et al. |
| 6,425,876 | B1 | 7/2002 | Frangi et al. |
| 6,432,067 | B1 | 8/2002 | Martin et al. |
| 6,443,894 | B1 | 9/2002 | Sumanaweera et al. |
| 6,453,526 | B2 | 9/2002 | Lorraine et al. |
| 6,488,639 | B1 | 12/2002 | Ribault et al. |
| 6,491,672 | B2 | 12/2002 | Slepian et al. |
| 6,494,848 | B1 | 12/2002 | Sommercorn et al. |
| 6,500,133 | B2 | 12/2002 | Martin et al. |
| 6,506,171 | B1 | 1/2003 | Vitek et al. |

(56) References Cited

U.S. PATENT DOCUMENTS

| | | | |
|---|---|---|---|
| 6,514,221 | B2 | 2/2003 | Hynynen et al. |
| 6,514,249 | B1 | 2/2003 | Maguire et al. |
| 6,520,915 | B1 | 2/2003 | Lin et al. |
| 6,522,926 | B1 | 2/2003 | Kieval et al. |
| 6,529,756 | B1 | 3/2003 | Phan |
| 6,548,047 | B1 | 4/2003 | Unger |
| 6,551,576 | B1 | 4/2003 | Unger et al. |
| 6,559,644 | B2 | 5/2003 | Froundlich et al. |
| 6,562,037 | B2 | 5/2003 | Paton et al. |
| 6,564,096 | B2 | 5/2003 | Mest |
| 6,565,557 | B1 | 5/2003 | Sporri et al. |
| 6,576,168 | B2 | 6/2003 | Hardcastle et al. |
| 6,584,360 | B2 | 6/2003 | Francischelli et al. |
| 6,593,574 | B2 | 7/2003 | Thomas et al. |
| 6,595,934 | B1 | 7/2003 | Hissong et al. |
| 6,599,256 | B1 | 7/2003 | Acker et al. |
| 6,599,288 | B2 | 7/2003 | Maguire et al. |
| 6,602,251 | B2 | 8/2003 | Burbank et al. |
| 6,612,988 | B2 | 9/2003 | Maor et al. |
| 6,616,624 | B1 | 9/2003 | Kieval |
| 6,626,855 | B1 | 9/2003 | Weng et al. |
| 6,633,658 | B1 | 10/2003 | Dabney et al. |
| 6,635,054 | B2 | 10/2003 | Fjield et al. |
| 6,648,883 | B2 | 11/2003 | Francischelli et al. |
| 6,652,461 | B1 | 11/2003 | Levkovitz |
| 6,656,131 | B2 | 12/2003 | Alster et al. |
| 6,656,136 | B1 | 12/2003 | Weng et al. |
| 6,669,655 | B1 | 12/2003 | Acker |
| 6,676,601 | B1 | 1/2004 | Lacoste et al. |
| 6,682,483 | B1 | 1/2004 | Abend et al. |
| 6,685,639 | B1 | 2/2004 | Wang et al. |
| 6,692,490 | B1 | 2/2004 | Edwards |
| 6,706,892 | B1 | 3/2004 | Ezrin et al. |
| 6,709,392 | B1 | 3/2004 | Salgo et al. |
| 6,709,407 | B2 | 3/2004 | Fatemi |
| 6,716,184 | B2 | 4/2004 | Vaezy et al. |
| 6,719,694 | B2 | 4/2004 | Weng et al. |
| 6,719,699 | B2 | 4/2004 | Smith |
| 6,719,755 | B2 | 4/2004 | Sliwa, Jr. et al. |
| 6,726,627 | B1 | 4/2004 | Lizzi et al. |
| 6,728,566 | B1 | 4/2004 | Subramanyan et al. |
| 6,735,461 | B2 | 5/2004 | Vitek et al. |
| 6,755,789 | B2 | 6/2004 | Stringer et al. |
| 6,763,722 | B2 | 7/2004 | Field et al. |
| 6,764,488 | B1 | 7/2004 | Burbank et al. |
| 6,837,886 | B2 | 1/2005 | Collins |
| 6,845,267 | B2 | 1/2005 | Harrison et al. |
| 6,846,291 | B2 | 1/2005 | Smith et al. |
| 6,875,176 | B2 | 4/2005 | Mourad et al. |
| 6,875,420 | B1 | 4/2005 | Quay |
| 6,905,498 | B2 | 6/2005 | Hooven |
| 6,932,771 | B2 | 8/2005 | Whitmore et al. |
| 6,954,977 | B2 | 10/2005 | Maguire |
| 6,955,648 | B2 | 10/2005 | Mozayeni et al. |
| 6,978,174 | B2 | 12/2005 | Gelfand et al. |
| 7,022,077 | B2 | 4/2006 | Mourad et al. |
| 7,052,463 | B2 | 5/2006 | Peszynski et al. |
| 7,052,695 | B2 | 5/2006 | Kalish |
| 7,063,666 | B2 | 6/2006 | Weng et al. |
| 7,128,711 | B2 | 10/2006 | Medan et al. |
| 7,149,564 | B2 | 12/2006 | Vining et al. |
| 7,156,816 | B2 | 1/2007 | Schwartz et al. |
| 7,162,303 | B2 | 1/2007 | Levin et al. |
| 7,211,060 | B1 | 5/2007 | Talish et al. |
| 7,260,250 | B2 | 8/2007 | Summers et al. |
| 7,285,093 | B2 | 10/2007 | Anisimov et al. |
| 7,371,231 | B2 | 5/2008 | Rioux et al. |
| 7,374,538 | B2 | 5/2008 | Nightingale et al. |
| 7,445,599 | B2 | 11/2008 | Kelly et al. |
| 7,470,241 | B2 | 12/2008 | Weng et al. |
| 7,499,748 | B2 | 3/2009 | Moffitt et al. |
| 7,510,536 | B2 | 3/2009 | Foley et al. |
| 7,530,958 | B2 | 5/2009 | Slayton et al. |
| 7,534,209 | B2 | 5/2009 | Abend et al. |
| 7,553,284 | B2 | 6/2009 | Vaitekunas |
| 7,617,005 | B2 | 11/2009 | Demarais et al. |
| 7,620,451 | B2 | 11/2009 | Demarais et al. |
| 7,621,873 | B2 | 11/2009 | Owen et al. |
| 7,628,764 | B2 | 12/2009 | Duarte et al. |
| 7,653,438 | B2 | 1/2010 | Deem et al. |
| 7,684,865 | B2 | 3/2010 | Aldrich et al. |
| 7,697,972 | B2 | 4/2010 | Verard et al. |
| 7,698,947 | B2 | 4/2010 | Sarr |
| 7,717,948 | B2 | 5/2010 | Demarais et al. |
| 7,725,184 | B2 | 5/2010 | Cazares |
| 7,766,833 | B2 | 8/2010 | Lee et al. |
| 7,783,358 | B2 | 8/2010 | Aldrich et al. |
| 7,942,871 | B2 | 5/2011 | Thapliyal et al. |
| 8,024,050 | B2 | 9/2011 | Libbus et al. |
| 8,025,688 | B2 | 9/2011 | Diederich et al. |
| 8,137,274 | B2 | 3/2012 | Weng et al. |
| 8,295,912 | B2 | 10/2012 | Gertner |
| 8,347,891 | B2 | 1/2013 | Demarais et al. |
| 8,383,671 | B1 | 2/2013 | Consigny |
| 8,447,414 | B2 | 5/2013 | Johnson et al. |
| 8,483,831 | B1 | 7/2013 | Hiavka et al. |
| 8,556,834 | B2 | 10/2013 | Gertner |
| 8,626,300 | B2 | 1/2014 | Demarais et al. |
| 8,702,619 | B2 | 4/2014 | Wang |
| 8,715,209 | B2 | 5/2014 | Gertner |
| 8,774,913 | B2 | 7/2014 | Demarais et al. |
| 8,790,281 | B2 | 7/2014 | Diederich et al. |
| 8,818,514 | B2 | 8/2014 | Zarins et al. |
| 8,845,629 | B2 | 9/2014 | Demarais et al. |
| 8,932,289 | B2 | 1/2015 | Mayse et al. |
| 9,022,948 | B2 | 5/2015 | Wang |
| 9,028,472 | B2 | 5/2015 | Mathur et al. |
| 9,066,720 | B2 | 6/2015 | Ballakur et al. |
| 9,072,902 | B2 | 7/2015 | Mathur et al. |
| 9,155,590 | B2 | 10/2015 | Mathur |
| 9,186,198 | B2 | 11/2015 | Demarais et al. |
| 9,186,212 | B2 | 11/2015 | Nabulovsky et al. |
| 9,234,878 | B2 | 1/2016 | Lavrentyev et al. |
| 9,289,132 | B2 | 3/2016 | Ghaffari |
| 9,326,816 | B2 | 5/2016 | Srivastava |
| 9,327,123 | B2 | 5/2016 | Yamasaki |
| 9,333,035 | B2 | 5/2016 | Rudie |
| 9,339,332 | B2 | 5/2016 | Srivastava |
| 9,345,530 | B2 | 5/2016 | Ballakur et al. |
| 9,375,154 | B2 | 6/2016 | Wang |
| 7,717,948 | C1 | 8/2016 | Demarais et al. |
| 9,427,579 | B2 | 8/2016 | Fain et al. |
| 9,439,598 | B2 | 9/2016 | Shimada et al. |
| 9,649,064 | B2 | 5/2017 | Toth et al. |
| 9,700,372 | B2 | 7/2017 | Schaer |
| 9,707,034 | B2 | 7/2017 | Schaer |
| 9,723,998 | B2 | 8/2017 | Wang |
| 9,730,639 | B2 | 8/2017 | Toth et al. |
| 9,743,845 | B2 | 8/2017 | Wang |
| 9,750,560 | B2 | 9/2017 | Ballakur et al. |
| 9,770,291 | B2 | 9/2017 | Wang et al. |
| 9,770,593 | B2 | 9/2017 | Gross |
| 9,801,684 | B2 | 10/2017 | Fain |
| 9,820,811 | B2 | 11/2017 | Wang |
| 9,907,983 | B2 | 3/2018 | Thapliyal et al. |
| 9,931,047 | B2 | 4/2018 | Srivastava |
| 9,943,666 | B2 | 4/2018 | Warnking |
| 9,956,034 | B2 | 5/2018 | Toth et al. |
| 9,968,790 | B2 | 5/2018 | Toth et al. |
| 9,981,108 | B2 | 5/2018 | Warnking |
| 9,999,463 | B2 | 6/2018 | Puryear et al. |
| 10,004,458 | B2 | 6/2018 | Toth et al. |
| 10,004,557 | B2 | 6/2018 | Gross et al. |
| 10,010,364 | B2 | 7/2018 | Harrington |
| 10,016,233 | B2 | 7/2018 | Pike |
| 10,022,085 | B2 | 7/2018 | Toth et al. |
| 10,039,901 | B2 | 8/2018 | Warnking |
| 10,123,903 | B2 | 11/2018 | Warnking et al. |
| 10,143,419 | B2 | 12/2018 | Toth et al. |
| 10,179,020 | B2 | 1/2019 | Ballakur et al. |
| 10,179,026 | B2 | 1/2019 | Ng |
| 10,182,865 | B2 | 1/2019 | Naga et al. |
| 10,226,633 | B2 | 3/2019 | Toth et al. |
| 10,230,041 | B2 | 3/2019 | Taylor et al. |

(56) References Cited

U.S. PATENT DOCUMENTS 10,245,429 B2 4/2019 Deem et al.
10,292,610 B2 5/2019 Srivastava
10,293,190 B2 5/2019 Zarins et al.
10,350,440 B2 7/2019 Taylor et al.
10,363,359 B2 7/2019 Toth et al.
10,368,775 B2 8/2019 Hettrick et al.
10,368,944 B2 8/2019 Schaer
10,376,310 B2 8/2019 Fain et al.
10,383,685 B2 8/2019 Gross et al.
10,398,332 B2 9/2019 Min et al.
10,456,605 B2 10/2019 Taylor et al.
10,470,684 B2 11/2019 Toth et al.
10,478,249 B2 11/2019 Gross et al.
10,499,937 B2 12/2019 Warnking
10,543,037 B2 1/2020 Shah
10,850,091 B2 12/2020 Zarins et al.
10,925,579 B2 * 2/2021 Zhang .................... G06T 7/246
11,357,447 B2 * 6/2022 Sverdlik ................ A61B 5/369
11,801,085 B2 10/2023 Wu et al.
12,133,765 B2 * 11/2024 Zhang .................. A61B 8/4254
2001/0014775 A1 8/2001 Koger et al.
2001/0014805 A1 8/2001 Burbank et al.
2001/0023365 A1 9/2001 Medhkour et al.
2001/0032382 A1 10/2001 Lorraine et al.
2001/0041910 A1 11/2001 McEwen
2001/0044636 A1 11/2001 Pedros et al.
2002/0042610 A1 4/2002 Sliwa, Jr. et al.
2002/0055736 A1 5/2002 Horn et al.
2002/0072672 A1 6/2002 Roundhill et al.
2002/0072741 A1 6/2002 Sliwa, Jr. et al.
2002/0095164 A1 7/2002 Andreas et al.
2002/0143275 A1 10/2002 Sarvazyan et al.
2002/0165535 A1 11/2002 Lesh
2002/0173724 A1 11/2002 Dorando et al.
2002/0193681 A1 12/2002 Vitek et al.
2002/0193831 A1 12/2002 Smith, III
2003/0004439 A1 1/2003 Pant et al.
2003/0009194 A1 1/2003 Saker et al.
2003/0010124 A1 1/2003 Bates
2003/0018255 A1 1/2003 Martin et al.
2003/0028111 A1 2/2003 Vaezy et al.
2003/0036771 A1 2/2003 McEwen et al.
2003/0050665 A1 3/2003 Ginn
2003/0060737 A1 3/2003 Brisken
2003/0069569 A1 4/2003 Burdette et al.
2003/0074039 A1 4/2003 Puskas
2003/0114756 A1 6/2003 Li
2003/0114878 A1 6/2003 Diederich et al.
2003/0120204 A1 6/2003 Unger et al.
2003/0125726 A1 7/2003 Maguire et al.
2003/0149366 A1 8/2003 Stringer et al.
2003/0153849 A1 8/2003 Huckle et al.
2003/0181963 A1 9/2003 Pellegrino et al.
2003/0187371 A1 10/2003 Vortman et al.
2003/0195420 A1 10/2003 Mendlein et al.
2003/0208101 A1 11/2003 Cecchi
2003/0216721 A1 11/2003 Diederich et al.
2003/0216792 A1 11/2003 Levin et al.
2003/0225331 A1 12/2003 Diederich et al.
2004/0002654 A1 1/2004 Davidson et al.
2004/0019349 A1 1/2004 Fuimaono et al.
2004/0030227 A1 2/2004 Littrup et al.
2004/0030268 A1 2/2004 Weng et al.
2004/0030269 A1 2/2004 Horn et al.
2004/0039280 A1 2/2004 Wu et al.
2004/0049105 A1 3/2004 Crutchfield et al.
2004/0054287 A1 3/2004 Stephens
2004/0054289 A1 3/2004 Eberle et al.
2004/0056200 A1 3/2004 Rothenfusser et al.
2004/0057492 A1 3/2004 Vona et al.
2004/0071664 A1 4/2004 McHale et al.
2004/0078034 A1 4/2004 Acker et al.
2004/0078219 A1 4/2004 Kaylor et al.
2004/0082859 A1 4/2004 Schaer
2004/0082978 A1 4/2004 Harrison et al.
2004/0089811 A1 5/2004 Lewis et al.
2004/0097805 A1 5/2004 Verard et al.
2004/0097819 A1 5/2004 Duarte
2004/0097840 A1 5/2004 Holmer
2004/0106880 A1 6/2004 Weng et al.
2004/0113524 A1 6/2004 Baumgartner et al.
2004/0122493 A1 6/2004 Ishibashi et al.
2004/0122494 A1 6/2004 Eggers et al.
2004/0127798 A1 7/2004 Dala-Krishna et al.
2004/0153126 A1 8/2004 Okai
2004/0158154 A1 8/2004 Hanafy et al.
2004/0181178 A1 9/2004 Aldrich et al.
2004/0210214 A1 10/2004 Knowlton
2004/0220167 A1 11/2004 Samiy
2004/0234453 A1 11/2004 Smith
2004/0242999 A1 12/2004 Vitek et al.
2004/0254620 A1 12/2004 Lacoste et al.
2004/0267252 A1 12/2004 Washington et al.
2005/0038339 A1 2/2005 Chauhan et al.
2005/0038340 A1 2/2005 Vaezy et al.
2005/0043625 A1 2/2005 Oliver et al.
2005/0046311 A1 3/2005 Baumgartner et al.
2005/0054955 A1 3/2005 Lidgren
2005/0065436 A1 3/2005 Ho et al.
2005/0070790 A1 3/2005 Niwa et al.
2005/0085793 A1 4/2005 Glossop
2005/0090104 A1 4/2005 Yang et al.
2005/0092091 A1 5/2005 Greelish
2005/0096538 A1 5/2005 Chomas et al.
2005/0096542 A1 5/2005 Weng et al.
2005/0119704 A1 6/2005 Peters et al.
2005/0149126 A1 7/2005 Libbus
2005/0154299 A1 7/2005 Hoctor et al.
2005/0159738 A1 7/2005 Visram et al.
2005/0165298 A1 7/2005 Larson et al.
2005/0182297 A1 8/2005 Gravenstein et al.
2005/0182319 A1 8/2005 Glossop
2005/0192638 A1 9/2005 Gelfand et al.
2005/0203501 A1 9/2005 Aldrich et al.
2005/0215990 A1 9/2005 Govari
2005/0228283 A1 10/2005 Gifford et al.
2005/0228459 A1 10/2005 Levin et al.
2005/0228460 A1 10/2005 Levin et al.
2005/0240102 A1 10/2005 Rachlin et al.
2005/0240103 A1 10/2005 Byrd et al.
2005/0240126 A1 10/2005 Foley et al.
2005/0240127 A1 10/2005 Seip et al.
2005/0240170 A1 10/2005 Zhang et al.
2005/0240241 A1 10/2005 Yun et al.
2005/0261672 A1 11/2005 Deem et al.
2005/0277853 A1 12/2005 Mast et al.
2005/0288730 A1 12/2005 Deem et al.
2006/0004417 A1 1/2006 Rossing et al.
2006/0025756 A1 2/2006 Francischelli et al.
2006/0041277 A1 2/2006 Deem et al.
2006/0052695 A1 3/2006 Adam et al.
2006/0052701 A1 3/2006 Carter et al.
2006/0058678 A1 3/2006 Vitek et al.
2006/0058707 A1 3/2006 Barthe et al.
2006/0058711 A1 3/2006 Harhen et al.
2006/0064081 A1 3/2006 Rosinko
2006/0082771 A1 4/2006 Doerrmann et al.
2006/0084966 A1 4/2006 Maguire et al.
2006/0118127 A1 6/2006 Chinn
2006/0122514 A1 6/2006 Byrd et al.
2006/0142827 A1 6/2006 Willard et al.
2006/0184069 A1 8/2006 Vaitekunas
2006/0217772 A1 9/2006 Libbus et al.
2006/0235286 A1 10/2006 Stone et al.
2006/0235300 A1 10/2006 Weng et al.
2006/0235303 A1 10/2006 Vaezy et al.
2006/0287681 A1 12/2006 Yonce et al.
2006/0293712 A1 12/2006 Kieval et al.
2007/0004984 A1 1/2007 Crum et al.
2007/0016113 A1 1/2007 Buchholtz et al.
2007/0016274 A1 1/2007 Boveja et al.
2007/0038115 A1 2/2007 Quigley et al.
2007/0055155 A1 3/2007 Owen et al.
2007/0055181 A1 3/2007 Deem et al.

(56) References Cited

U.S. PATENT DOCUMENTS

| | | | |
|---|---|---|---|
| 2007/0060921 | A1 | 3/2007 | Janssen et al. |
| 2007/0066957 | A1 | 3/2007 | Demarais et al. |
| 2007/0072741 | A1 | 3/2007 | Robideau |
| 2007/0106292 | A1 | 5/2007 | Kaplan |
| 2007/0106339 | A1 | 5/2007 | Errico et al. |
| 2007/0112327 | A1 | 5/2007 | Yun et al. |
| 2007/0129720 | A1 | 6/2007 | Demarais et al. |
| 2007/0129761 | A1 | 6/2007 | Demarais et al. |
| 2007/0135875 | A1 | 6/2007 | Demarais et al. |
| 2007/0142879 | A1 | 6/2007 | Greenberg et al. |
| 2007/0149880 | A1 | 6/2007 | Willis |
| 2007/0167806 | A1 | 7/2007 | Wood et al. |
| 2007/0179379 | A1 | 8/2007 | Weng et al. |
| 2007/0203527 | A1 | 8/2007 | Ben-David et al. |
| 2007/0213616 | A1 | 9/2007 | Anderson et al. |
| 2007/0233185 | A1 | 10/2007 | Anderson et al. |
| 2007/0239000 | A1 | 10/2007 | Emery et al. |
| 2007/0265687 | A1 | 11/2007 | Deem et al. |
| 2007/0282407 | A1 | 12/2007 | Demarais et al. |
| 2008/0030104 | A1 | 2/2008 | Prus |
| 2008/0033292 | A1 | 2/2008 | Shafran |
| 2008/0033420 | A1 | 2/2008 | Nields et al. |
| 2008/0039746 | A1 | 2/2008 | Hissong et al. |
| 2008/0045864 | A1 | 2/2008 | Candy et al. |
| 2008/0045865 | A1 | 2/2008 | Kislev |
| 2008/0046016 | A1 | 2/2008 | Ben-David et al. |
| 2008/0047325 | A1 | 2/2008 | Bartlett |
| 2008/0051767 | A1 | 2/2008 | Rossing et al. |
| 2008/0058683 | A1 | 3/2008 | Gifford et al. |
| 2008/0194954 | A1 | 8/2008 | Unger et al. |
| 2008/0200806 | A1 | 8/2008 | Liu et al. |
| 2008/0200815 | A1 | 8/2008 | Van Der Steen |
| 2008/0215031 | A1 | 9/2008 | Belfort et al. |
| 2008/0234569 | A1 | 9/2008 | Ti et al. |
| 2008/0255498 | A1 | 10/2008 | Houle |
| 2008/0255642 | A1 | 10/2008 | Zarins et al. |
| 2008/0261009 | A1 | 10/2008 | Kawabata |
| 2008/0288017 | A1 | 11/2008 | Kieval et al. |
| 2008/0312561 | A1 | 12/2008 | Chauhan |
| 2008/0312562 | A1 | 12/2008 | Routh et al. |
| 2008/0317204 | A1 | 12/2008 | Sumanaweera et al. |
| 2008/0319375 | A1 | 12/2008 | Hardy |
| 2009/0000382 | A1 | 1/2009 | Sathish et al. |
| 2009/0012098 | A1 | 1/2009 | Jordan et al. |
| 2009/0036948 | A1 | 2/2009 | Levin et al. |
| 2009/0054770 | A1 | 2/2009 | Daigle |
| 2009/0062697 | A1 | 3/2009 | Zhang et al. |
| 2009/0062873 | A1 | 3/2009 | Wu et al. |
| 2009/0076409 | A1 | 3/2009 | Wu et al. |
| 2009/0088623 | A1 | 4/2009 | Vortman et al. |
| 2009/0099627 | A1 | 4/2009 | Molnar et al. |
| 2009/0112095 | A1 | 4/2009 | Daigle |
| 2009/0112133 | A1 | 4/2009 | Deisseroth et al. |
| 2009/0137873 | A1 | 5/2009 | Mitsuhashi |
| 2009/0149782 | A1 | 6/2009 | Cohen |
| 2009/0163982 | A1 | 6/2009 | Decharms |
| 2009/0221908 | A1 | 9/2009 | Glossop |
| 2009/0221939 | A1 | 9/2009 | Demarais et al. |
| 2009/0234407 | A1 | 9/2009 | Hastings et al. |
| 2009/0247911 | A1 | 10/2009 | Novak et al. |
| 2009/0248005 | A1 | 10/2009 | Rusin et al. |
| 2009/0264755 | A1 | 10/2009 | Chen et al. |
| 2009/0306644 | A1 | 12/2009 | Mayse et al. |
| 2009/0315978 | A1 | 12/2009 | Wurmlin et al. |
| 2010/0010393 | A1 | 1/2010 | Duffy et al. |
| 2010/0022921 | A1 | 1/2010 | Seip et al. |
| 2010/0023088 | A1 | 1/2010 | Stack et al. |
| 2010/0042020 | A1 | 2/2010 | Ben-Ezra |
| 2010/0081971 | A1 | 4/2010 | Allison |
| 2010/0092424 | A1 | 4/2010 | Sanghvi et al. |
| 2010/0125269 | A1 | 5/2010 | Emmons et al. |
| 2010/0128141 | A1 | 5/2010 | Jang |
| 2010/0160781 | A1 | 6/2010 | Carter et al. |
| 2010/0172567 | A1 | 7/2010 | Prokoski |
| 2010/0174188 | A1 | 7/2010 | Wang et al. |
| 2010/0286522 | A1 | 11/2010 | Beach et al. |
| 2011/0021913 | A1 | 1/2011 | Weng et al. |
| 2011/0028867 | A1 | 2/2011 | Choo et al. |
| 2011/0060255 | A1 | 3/2011 | Chen |
| 2011/0092781 | A1 | 4/2011 | Gertner |
| 2011/0092880 | A1 | 4/2011 | Gertner |
| 2011/0112400 | A1 | 5/2011 | Emery et al. |
| 2011/0118723 | A1 | 5/2011 | Turner et al. |
| 2011/0118805 | A1 | 5/2011 | Wei et al. |
| 2011/0124976 | A1 | 5/2011 | Sabczynski et al. |
| 2011/0125206 | A1 | 5/2011 | Bornzin |
| 2011/0208096 | A1 | 8/2011 | Demarais et al. |
| 2011/0234834 | A1 | 9/2011 | Sugimoto |
| 2011/0251489 | A1 | 10/2011 | Zhang et al. |
| 2011/0257523 | A1 | 10/2011 | Hastings et al. |
| 2011/0257561 | A1 | 10/2011 | Gertner et al. |
| 2011/0260965 | A1 | 10/2011 | Kim et al. |
| 2011/0319765 | A1 | 12/2011 | Gertner et al. |
| 2012/0004656 | A1 | 1/2012 | Jackson et al. |
| 2012/0016239 | A1 | 1/2012 | Barthe et al. |
| 2012/0065492 | A1 | 3/2012 | Gertner et al. |
| 2012/0071757 | A1 | 3/2012 | Salcudean |
| 2012/0109018 | A1 | 5/2012 | Gertner et al. |
| 2012/0116383 | A1* | 5/2012 | Mauch .............. A61M 25/0138 606/33 |
| 2012/0123243 | A1 | 5/2012 | Hastings |
| 2012/0265198 | A1 | 10/2012 | Crow et al. |
| 2012/0296232 | A1 | 11/2012 | Ng |
| 2013/0023897 | A1 | 1/2013 | Wallace |
| 2013/0085489 | A1 | 4/2013 | Fain et al. |
| 2013/0094729 | A1* | 4/2013 | Mauldin, Jr. ........ A61B 8/5207 382/128 |
| 2013/0096550 | A1 | 4/2013 | Hill |
| 2013/0116737 | A1 | 5/2013 | Edwards et al. |
| 2013/0120552 | A1 | 5/2013 | Yamanaka et al. |
| 2013/0123770 | A1 | 5/2013 | Smith |
| 2013/0131743 | A1 | 5/2013 | Yamasaki et al. |
| 2013/0150749 | A1 | 6/2013 | McLean et al. |
| 2013/0165925 | A1 | 6/2013 | Mathur et al. |
| 2013/0172872 | A1 | 7/2013 | Subramaniam |
| 2013/0245429 | A1 | 9/2013 | Zhang et al. |
| 2013/0261688 | A1 | 10/2013 | Dong |
| 2013/0274614 | A1 | 10/2013 | Shimada et al. |
| 2013/0289369 | A1 | 10/2013 | Margolis |
| 2013/0289682 | A1 | 10/2013 | Barman et al. |
| 2014/0005477 | A1 | 1/2014 | Gupta et al. |
| 2014/0018788 | A1 | 1/2014 | Engelman et al. |
| 2014/0043933 | A1 | 2/2014 | Belevich et al. |
| 2014/0058294 | A1 | 2/2014 | Gross et al. |
| 2014/0086684 | A1 | 3/2014 | Sehr et al. |
| 2014/0163540 | A1 | 6/2014 | Schaer |
| 2014/0171782 | A1 | 6/2014 | Bruder et al. |
| 2014/0257271 | A1 | 9/2014 | Mayse et al. |
| 2014/0274614 | A1 | 9/2014 | Min et al. |
| 2014/0275705 | A1 | 9/2014 | Virshup et al. |
| 2014/0275924 | A1 | 9/2014 | Min et al. |
| 2014/0288551 | A1 | 9/2014 | Bharmi et al. |
| 2014/0288616 | A1 | 9/2014 | Rawat et al. |
| 2014/0303617 | A1 | 10/2014 | Shimada |
| 2014/0316269 | A1 | 10/2014 | Zhang et al. |
| 2014/0331771 | A1 | 11/2014 | Baba et al. |
| 2015/0005613 | A1 | 1/2015 | Kim et al. |
| 2015/0005637 | A1 | 1/2015 | Stegman |
| 2015/0029819 | A1 | 1/2015 | Yacoubian |
| 2015/0045604 | A1* | 2/2015 | Sawkey ............... A61N 5/1068 600/1 |
| 2015/0080926 | A1* | 3/2015 | Emery ..................... A61N 7/02 606/169 |
| 2015/0092814 | A1 | 4/2015 | Wolfgruber |
| 2015/0175747 | A1 | 6/2015 | Liu et al. |
| 2015/0231414 | A1 | 8/2015 | Ein-Gal |
| 2015/0253266 | A1 | 9/2015 | Lucon et al. |
| 2015/0289931 | A1 | 10/2015 | Puryear et al. |
| 2016/0000345 | A1 | 1/2016 | Kobayashi et al. |
| 2016/0045121 | A1 | 2/2016 | Akingba et al. |
| 2016/0109393 | A1 | 4/2016 | Mandelis et al. |
| 2016/0121142 | A1 | 5/2016 | Zhang et al. |
| 2016/0247279 | A1* | 8/2016 | Lavi ...................... G06T 7/0014 |
| 2016/0299108 | A1 | 10/2016 | Bisle et al. |

(56) References Cited

U.S. PATENT DOCUMENTS

| | | | |
|---|---|---|---|
| 2016/0317122 | A1 | 11/2016 | Dossantos |
| 2017/0027460 | A1 | 2/2017 | Shimada et al. |
| 2017/0035310 | A1 | 2/2017 | Shimada et al. |
| 2017/0097280 | A1 | 4/2017 | Drescher et al. |
| 2017/0212066 | A1 | 7/2017 | Thompson et al. |
| 2017/0296264 | A1 | 10/2017 | Wang |
| 2018/0022108 | A1 | 1/2018 | Mori et al. |
| 2018/0042670 | A1 | 2/2018 | Wang et al. |
| 2018/0064359 | A1 | 3/2018 | Pranaitis |
| 2018/0078307 | A1 | 3/2018 | Wang et al. |
| 2018/0185091 | A1 | 7/2018 | Toth et al. |
| 2018/0221087 | A1 | 8/2018 | Puryear et al. |
| 2018/0249958 | A1 | 9/2018 | Toth et al. |
| 2018/0250054 | A1 | 9/2018 | Gross et al. |
| 2018/0280082 | A1 | 10/2018 | Puryear et al. |
| 2018/0289320 | A1 | 10/2018 | Toth et al. |
| 2018/0310991 | A1 | 11/2018 | Pike |
| 2018/0333204 | A1 | 11/2018 | Ng |
| 2019/0046111 | A1 | 2/2019 | Toth et al. |
| 2019/0046264 | A1 | 2/2019 | Toth et al. |
| 2019/0076191 | A1 | 3/2019 | Wang |
| 2019/0110704 | A1 | 4/2019 | Wang |
| 2019/0134396 | A1 | 5/2019 | Toth et al. |
| 2019/0151670 | A1 | 5/2019 | Toth et al. |
| 2019/0183560 | A1 | 6/2019 | Ballakur et al. |
| 2019/0307361 | A1 | 10/2019 | Hettrick et al. |
| 2020/0046248 | A1 | 2/2020 | Toth et al. |
| 2020/0077907 | A1 | 3/2020 | Shimada et al. |

FOREIGN PATENT DOCUMENTS

| | | |
|---|---|---|
| EP | 0679371 | 11/1995 |
| EP | 1265223 | 12/2002 |
| EP | 1299035 | 4/2003 |
| EP | 1503685 | 2/2005 |
| EP | 1579889 | 9/2005 |
| EP | 1847294 | 10/2007 |
| EP | 2359764 | 8/2011 |
| EP | 2430996 | 3/2012 |
| EP | 2842604 | 3/2015 |
| EP | 2968984 | 1/2016 |
| EP | 2995250 | 3/2016 |
| EP | 3799931 | 4/2021 |
| JP | H05220152 | 8/1993 |
| JP | 2007000218 | 1/2007 |
| WO | WO95/02361 | 1/1995 |
| WO | WO97/31364 | 8/1997 |
| WO | WO1999/002096 | 1/1999 |
| WO | WO99/48621 | 9/1999 |
| WO | WO01/34018 | 5/2001 |
| WO | WO2001/095820 | 12/2001 |
| WO | WO2002/005897 | 1/2002 |
| WO | WO2002/019934 | 3/2002 |
| WO | WO2003/022167 | 3/2003 |
| WO | WO2003/051450 | 6/2003 |
| WO | WO02/069805 | 4/2005 |
| WO | WO2005/030295 | 4/2005 |
| WO | WO2006/003606 | 1/2006 |
| WO | WO2006/041881 | 4/2006 |
| WO | WO2006/060053 | 6/2006 |
| WO | WO2006/121447 | 11/2006 |
| WO | WO2006/129099 | 12/2006 |
| WO | WO2007/014003 | 2/2007 |
| WO | WO2008/144274 | 11/2008 |
| WO | WO2009/003138 | 12/2008 |
| WO | WO2009/018351 | 2/2009 |
| WO | WO2009/018394 | 2/2009 |
| WO | WO2009/081339 | 7/2009 |
| WO | WO2011/053757 | 5/2011 |
| WO | WO2011/053772 | 5/2011 |
| WO | WO2014/164363 | 10/2014 |

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

Ahmed, Muneeb et al., "Thermal Ablation Therapy for Hepatocellular Carcinoma," J. Vasc. Interv, Radiol., vol. 13, No. 9 pt. 2, 2002.

American Heart Association—Pulmonary Hypertension: High Blood Pressure in the Heart-to-Lung System, (last reviewed Oct. 31, 2016).

Appeal Brief of Patent Owner from Reexamination 95-002,110.

Aytac, et al., "Correlation Between the Diameter of the Main Renal Artery and the Presence of an Accessory Renal Artery", J Ultrasound Med 22:433-439, 2003.

Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).

Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.

Benito, Fernando et al., "Radiofrequency catheter ablation of accessory pathways in infants," Heart, vol. 78, p. 160-162, 1997.

Berjano, E. et al., "A Cooled Intraesophageal Balloon to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised Symplicity HTN-3 Trial, 400 Lancet 1405 (2022).

Billard, B.E. et al., Effects of Physical Parameters on High Temperature Ultrasound Hyperthermia, Ultrasound in Med. & Biol. Vol. 16, No. 4, pp. 409-420, 1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.

Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).

Bush, et al., "Endovascular revascularization of renal artery stenosis: Technical and clinical results", Journal of Vascular Surgery, May 2001, 1041-1049 (2001).

Calkins, Hugh et al., "Temperature Monitoring During Radiofrequency Catheter Ablation Procedures Using Closed Loop Control," Circulation vol. 90, No. 3, p. 1279-1286, Sep. 1994.

Camasao, D. B. et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

(56) References Cited

OTHER PUBLICATIONS

Carter, Stefan et al., Measurement of Renal Artery Pressures by Catheterization in Patients with and without Renal Artery Stenosis, Circulation, vol. XXXIII, 443-449 (1966).
Chang, Isaac A. et al., "Thermal Modeling of Lesion Growth with Radiofrequency Ablation Devices," Biomedical Engineering Online vol. 3, p. 27, 2004.
Chapelon, J.Y., "Treatment of Localised Prostate Cancer with Transrectal High Intensity Focused Ultrasound," European Journal of Ultrasound 9, 31-38, 1999.
Charlesworth, Peter et al., Renal Artery Injury from a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022, in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Chung, Andrew et al., "Thermal dosimetry of a focused ultrasound beam in vivo by magnetic resonance imaging," Medical Physics, vol. 26, No. 9, p. 2017-2026, Sep. 1999.
Coates, Paul et al., "Time, Temperature, Power, and Impedance Considerations for Radiofrequency Catheter Renal Denervation," Cardiovascular Revascularization Medicine 42, 171-177 (2022).
Corrected Patent Owner's Response to Office Action, dated May 10, 2013, from File History of Inter Partes Reexamination 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty.
Curriculum Vitae of Dr. Michael Bohm.
Curriculum Vitae of Farrell Mendelsohn.
Damianou, Christakis et al., "High Intensity Focused Ultrasound Ablation of Kidney Guided MRI," Ultrasound in Med. & Biol., vol. 30, No. 3, p. 397-404, 2004.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Cooling for Interstitial Thermal Therapy, SPIE vol. 3594, 36-46, Jan. 1999.
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170 -178, Jan. 2000.
Deardorff, Dana L. et al., "Control of interstitial thermal coagulation: Comparative evaluation of microwave and ultrasound applicators," Medical Physics vol. 28, No. 1, p. 104-117, Jan. 2001.
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Dr. Michael Bohm dated Sep. 29, 2022, on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Declaration of Jonathan Bradford dated May 10, 2022, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Defendant's Reply to Court Order of Oct. 4, 2022, and Plaintiff's Surrejoinder of Sep. 29, 2022 in the Mannheim District Court, case No. 7 O 14/21, dated Oct. 31, 2022.
Defendant's Response dated May 11, 2022, in the Munich Federal Patent Court, Nullity Suit 6 Ni 32/22.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Dibona, Gerald F. et al., "Neural Control of Renal Function", 77 Physiological Reviews No. 1, 75 (1997).
Dibona, Gerald F., "Neural Control of the Kidney, Past, Present and Future," 41 [Part II] Hypertension 621 24 (2003).
Dibona, Gerald, "Sympathetic Nervous System and Kidney in Hypertension", Current Opinion in Nephrology and Hypertension, vol. 11, 197-200 (2002).
Diederich, Chris J. et al., "Ultrasound Technology for Hyperthermia," Ultrasound in Med. & Biol., vol. 25, No. 6, p. 871-887, 1999.
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002.807323.
Dinerman, Jay L. et al., "Temperature Monitoring During Radiofrequency Ablation," Journal of Cardiovascular Electrophysiology, vol. 7 No. 2, p. 163-173, Feb. 1996.
Draney, Mary et al., Three-Dimensional Analysis of Renal Artery Bending Motion During Respiration, International Society of Endovascular Specialists, vol. 12, 380-386 (2005).
EP Board of Appeals Communication dated Dec. 17, 2019—Preliminary Remarks for EP appeal No. T2680/16-3.3.4.01.
Erikson, Kenneth et al., Ultrasound in Medicine: A Review, IEEE Transactions on Sonics and Ultrasonics, vol. 21, No. 3 (1974).
Esler, Murray et al., "The future of renal denervation," Autonomic Neuroscience: Basic and Clinical, vol. 204, p. 131-138, May 2017.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 12180431.4 dated Jan. 17, 2013.
European Search Report in Application No. 20202272.9 dated Mar. 1, 2021.
European Search Report in Application No. 218186547 dated Nov. 19, 2018.

(56) References Cited

OTHER PUBLICATIONS

Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (Radiosound-HTN), 139 Circulation 590 (2019).
File History to EP1802370B1 Part 1.
File History to EP1802370B1 Part 2.
File History to EP1802370B1 Part 3.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Fry, F.J. et al., "Production of Reversible Changes in the Central Nervous System by Ultrasound," Science, vol. 127, p. 83-84, Jan. 1958.
Fry, Frank J., "Precision High Intensity Focusing Ultrasonic Machines for Surgery," High Intensity Focused U.S., 152-156, Sep. 6-7, 1957.
Fry, William J., "Action of Ultrasound on Nerve Tissue—A review," The Journal of the Acoustical Society of America, vol. 25 No. 1, p. 1-5, Jan. 1953.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Graham, S.J. et al., "Quantifying Tissue Damage Due to Focused Ultrasound Heating Observed by MRI" Magnetic Resonance in Medicine vol. 41, p. 321-328, 1999.
Gray, Henry, Gray's Anatomy: The Anatomical Basis of Medicine and Surgery, Churchill Livingstone, New York, NY (1995).
Habicht, Antje et al., Sympathetic Overactivity and Kidneys, The Middle European Journal of Medicine, vol. 115, 634-640 (2003).
Häcker, Axel et al., "Extracorporeal Organotripsy for Renal Tumours," Current Opinion in Urology, vol. 13, p. 221-225, 2003.
Haines, David, "Biophysics of Ablation: Application to Technology," Journal of Cardiovascular Electrophysiology, vol. 15, No. 10, p. S2-S11, Oct. 2004.
Hansen et al., The Transplanted Human Kidney Does Not Achieve Functional Reinnervation, 87 Clinical Science 13 (1994).
Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
Hausberg, Martin et al., "Sympathetic Nerve Activity in End-Stage Renal Disease," Circulation, vol. 106, p. 1974-1979, 2002.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1958, 1 1 pages.
Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, et al., Renal Denervation Prevents and Reverses Hyperinsulinemia-Induced Hypertension in Rats, Hypertension 32 (1998) pp. 249-254.
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Institution Decision Granting Institution of Inter Partes Review 35 U.S.C. sec. 314, dated Aug. 8, 2022, in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Israel, Gary M. et al., "MRI of the Kidney and Urinary Tract," Journal of Magnetic Resonance Imaging, vol. 24, p. 725-734, 2006.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Jiang, S.C. et al., "Effects of Thermal Properties and Geometrical Dimensions on Skin Burn Injuries," Burns, vol. 28, p. 713-717, 2002.
Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.
Kaltenbach, Benjamin et al., Renal Artery Stenosis After Renal Sympathetic Denervation, Journal of the American College of Cardiology, vol. 60, No. 25 (2012).
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, Massdevice (Dec. 6, 2016).

(56) References Cited

OTHER PUBLICATIONS

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. Oct. 10, 2003.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lauder, Lucas et al., "Renal Denervation in the Management of Hypertension," EuroIntervention, vol. 20, p. e467-e478, 2024.
Lee, Jong Deok et al., MR imaging-histopathologic correlation of radiofrequency thermal ablation lesion in a rabbit liver model: observation during acute and chronic stages, 2 Korean J. Radiol. 151 (2001).
Lele, P.P., "Effects of Focused Ultrasonic Radiation on Peripheral Nerve, with Observations on Local Heating," Experimental Neurology, vol. 8, p. 47-83,1963.
Levin, S., et al., ARDIAN: Succeeding Where Drugs Fail—Treating Hypertension in the Cath Lab, In Vivo, 27:23 (2009).
Lewis, Matthew A. et al., "Thermometry and Ablation Monitoring with Ultrasound," Int. J. Hyperthermia vol. 31, Issue 2, p. 163-181, Mar. 2015.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Liu, Xinmeng et al., "Visualization and mapping of the right phrenic nerve by intracardiac echocardiography during atrial fibrillation ablation," Europace vol. 25, p. 1352-1360, 2023.
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Mahfoud, Felix et al., "Device Therapy of Hypertension," Circulation Research nol. 128, p. 1080-1099, Apr. 2021.
Mahfoud, Felix et al., Catheter-Based Renal Denervation is No Simple Matter: Lessons to be Learned From Our Anatomy?, Journal of the American College of Cardiology, vol. 64, No. 7, 644-647 (2014).
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue vols. Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Marine, Joseph E., Catheter ablation therapy for supraventricular arrhythmias, 298 JAMA 2768 (2007).
Martin, Louis K. et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Inc., Renal Denervation (RDN): Novel Catheter-Based Treatment for Hypertension, Scientific Background, 2011.
Medtronic Inc., The Symplicity RDN System, 2012.
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic, Symplicity RDN Common System Q&A.
Mendelsohn, Farrell O., "Microanatomy of the Renal Sympathetic Nervous System," Endovascular Today, p. 59-62, Oct. 2013.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function in Renal Failure and Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., "First Human Experience with Pulmonary Vein Isolation Using a Through-the-Balloon Circumferential Ultrasound Ablation System for Recurrent Atrial Fibrillation", Circulation, vol. 102, 1879-1882 (2000).
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H et al., "MRI-Guided Interstitial Ultrasound Thermal Therapy of the Prostate: A Feasibility Study in the Canine Model," Medical Physics vol. 32, No. 3, p. 733-743, Mar. 2005.
Netter, Frank, Atlas of Human Anatomy, Icon Learning Systems, Rochester, NY (2002).
Neumann, Jutta, "Sympathetic hyperactivity in chronic kidney disease: Pathogenesis, clinical relevance, and treatment", International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation with Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.

(56) References Cited

OTHER PUBLICATIONS

Notice of Deposition of Tucker, filed Dec. 30, 2022, in the Patent Trial and Appeal Board, United States Patent and Trademark Office, Petition No. PTAB-IPR2022-00431.
Notice of Deposition of van der Weide, filed Dec. 30, 2022, in the Patent Trial and Appeal Board, United States Patent and Trademark Office, Petition No. PTAB-IPR2022-00431.
Notice re filing date accorded, dated Feb. 10, 2022, in the Patent Trial and Appeal Board, United States Patent and Trademark Office, Petition No. PTAB-IPR2022-00431.
Nozawa, T., et al. "Effects of long-term renal sympathetic denervation on heart failure after myocardial infarction in rats." Heart Vessels, 16:51-56 (2002).
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Okamura, Keisuke et al., "Intravascular Ultrasound Can be Used to Locate Nerves, but not Confirm Ablation, During Renal Sympathetic Denervation," J. Clin. Med. Res., vol. 13, No. 12, p. 556-562, 2021.
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order Setting Oral Hearing 37 C.F.R. § 42.70, dated Mar. 24, 2023, in the Patent Trial and Appeal Board, United States Patent and Trademark Office, Petition No. PTAB-IPR2022-00431.
Order: Conduct of the Proceeding Scheduling Order 37 C.F.R. sec. 42.5, dated Aug. 8, 2022, in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on Patients Suffering from Nephritis, 14 J. Clinical Investigation 443 (1935).
Page, Irvine H. & George J. Heuer, The Effect of Renal Denervation on the Level of Arterial Blood Pressure and Renal Function in Essential Hypertension, 14 J. Clinical Investigation 27 (1935).
Papademetriou, et al., "Renal Sympathetic Denervation: Hibernation or Resurrection?", Cardiology 2016; 135, 11 pgs.
Papademetriou, Vasilios et al., "Renal Nerve Ablation for Resistant Hypertension, How Did We Get Here, Present Status, and Future Directions," Circulation, No. 129, p. 1440-1451, 2014.
Papademetriou, Vasilios et al., Renal Sympathetic Denervation for the Treatment of Difficult-to-Control or Resistant Hypertension, 2011 Int. J. Hypertension, Article 196518 (2011).
Papadopoulos, N., "Evaluation of a Small Flat Rectangular Therapeutic Ultrasonic Transducer Intended for Intravascular Use," Ultrasonics 74, 196-203, 2017.
Pappone C, et al., "Circumferential radiofrequency ablation of pulmonary vein ostia: a new anatomic approach for curing atrial fibrillation", Circulation. 2000; 102(21): 2619-2628. (2000).
Patent Owner Medtronic Ireland Power of Attorney, filed May 10, 2022, in the Patent Trial and Appeal Board, United States Patent and Trademark Office, Petition No. PTAB-IPR2022-00431.
Patent Owner's Amended Objections to Evidence Under 37 C.F.R. §42.64.
Patent Owner's Mandatory Notice, filed Feb. 3, 2022, in the Patent Trial and Appeal Board, United States Patent and Trademark Office, Petition No. PTAB-IPR2022-00431.
Patent Owner's Notice of Deposition of Dr. Chris Daft filed Feb. 21, 2023, in the Patent Trial and Appeal Board, United States Patent and Trademark Office, Petition No. PTAB-IPR2022-00431.
Patent Owner's Notice of Deposition of Dr. Chris Daft, filed Sep. 20, 2022, in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022, in the Patent Trial and Appeal Board, United States Patent and Trademark Office, Petition No. PTAB-IPR2022-00431.
Patent Owner's Notice of Deposition of Dr. John Moriarty, filed Feb. 21, 2023, in the Patent Trial and Appeal Board, United States Patent and Trademark Office, Petition No. PTAB-IPR2022-00431.
Patent Owner's Objections to Evidence, filed Aug. 18, 2022, in the Patent Trial and Appeal Board, United States Patent and Trademark Office, Petition No. PTAB-IPR2022-00431.
Patent Owner's Power of Attorney, filed Feb. 3, 2022, in the Patent Trial and Appeal Board, United States Patent and Trademark Office, Petition No. PTAB-IPR2022-00431.
Patent Owner's Preliminary Response, filed May 10, 2022, in the Patent Trial and Appeal Board, United States Patent and Trademark Office, Petition No. PTAB-IPR2022-00431.
Patent Owner's Request for Oral Hearing, filed Mar. 23, 2023, in the Patent Trial and Appeal Board, United States Patent and Trademark Office, Petition No. PTAB-IPR2022-00431.
Patent Owner's Response, filed Oct. 27, 2022, in the Patent Trial and Appeal Board, United States Patent and Trademark Office, Petition No. PTAB-IPR2022-00431.
Patent Owner's Sur-Reply, filed Mar. 9, 2023, in the Patent Trial and Appeal Board, United States Patent and Trademark Office, Petition No. PTAB-IPR2022-00431.
Patent Owner's Updated Mandatory Notice, filed May 10, 2022, in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022, by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner Reply, filed Jan. 23, 2022, in the Patent Trial and Appeal Board, United States Patent and Trademark Office, Petition No. PTAB-IPR2022-00431.
Petitioner's Power of Attorney for Otsuka Medical Devices Co., Ltd., filed Jan. 13, 2022, in the Patent Trial and Appeal Board, United States Patent and Trademark Office, Petition No. PTAB-IPR2022-00431.
Petitioner's Power of Attorney for Recor Medical, Inc., filed Jan. 13, 2022, in the Patent Trial and Appeal Board, United States Patent and Trademark Office, Petition No. PTAB-IPR2022-00431.
Petitioners' Request for Oral Argument, filed Mar. 21, 2023, in the Patent Trial and Appeal Board, United States Patent and Trademark Office, Petition No. PTAB-IPR2022-00431.
Petitioners' Updated Mandatory Notices, dated Jan. 18, 2022, in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022, Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022, in Mannheim District Court, Infringement suit 7 O 147/21.
Plaintiff's Technical Brief dated Sep. 29, 2022, in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Pozzoli, Alberto et al., "Electrophysiological Efficacy of Epicor High-Intensity Focused Ultrasound," European Journal of Cardio-Thoracic surgery, vol. 42, p. 129-134, 2012.
Prakash, Punit, et al., "Considerations for Theoretical Modeling of Thermal Ablation with Catheter-Based Ultrasonic Sources: Impli-

(56) References Cited

OTHER PUBLICATIONS cations for Treatment Planning, Monitoring and Control," International Journal of Hyperthermia, 28:1, 69-86.
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut, et al., Martin, Pulmonary vein stenosis following catheter ablation of atrial fibrillation, 20 Curr. Opin. Cardiol. 484 (2005).
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Quadri, Syed A. et al., "High-intensity focused ultrasound: past, present, and future in neurosurgery," Neurosurgical Focus, vol. 44, No. 2, p. 1-9, Feb. 2018.
Reaz, M.B.I., et al., "Techniques of EMG signal analysis: detection, processing, classification and applications," Biological Procedures Online, Jan. 2006, 25 pages.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Riis, Thomas et al., "Effective Ultrasonic Stimulation in Human Peripheral Nervous System," IEEE Trans. Biomed. Eng. Jan. 2022; 69(1): 15-22.
Romanes, G.J., Cunningham's Textbook of Anatomy (11th ed. 1972).
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Roux, N. et al., "The Myocardial Sleeves of the Pulmonary Veins: Potential Implications for Atrial Fibrillation," Surg. Radiol. Anat., vol. 26, p. 285-289, Feb. 2004.
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Ryan, Thomas P., Thermal Treatment of Tissue with Image Guidance; Ultrasound Catheters for Circumferential Cardiac Ablation 1999.
Sakakura, Kenichi et al., Anatomic Assessment of Sympathetic Peri-Arterial Renal Nerves in Man, Journal of the American College of Cardiology, vol. 64, No. 7, 635-643 (2014).
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Salmanpour, A., et al., "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1109/ICASSP.2010.5495604.
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Sanghvi, Kintur et al., "Rationale and design for studies of renal denervation in the absence (SPYRAL HTN Off-Med) and presence (SPYRAL HTN On-Med) of antihypertensive medications," American Heart Journal, vol. 180, p. e1-e2. Oct. 2016.
Sato, Yu, et al., "Translational Value of Preclinical Models for Renal Denervation: a histological comparison of human versus porcine renal nerve anatomy," EuroIntervention, 18, e1120-e1128, 2023.
Satou, Shunsuke et al., "Observation of renal sympathetic nerves by intravascular ultrasound," Hypertension Research vol. 42, p. 1092-1094, 2019.
Schlaich, M.P. et al., "Renal Denervation: A Potential New Treatment Modality for Polycystic Ovary Syndrome," Journal of Hypertension, vol. 29, No. 5, pp. 991-996 2011. doi:10.1097/HJH.0b013e328344db3a.
Schmidt, Boris et al., "Balloon Catheters for Pulmonary Vein Isolation," Herz vol. 33, p. 580-584, 2008.
Schmidt, Boris, et al., "Pulmonary Vein Isolation by High Intensity Focused Ultrasound," Indian Pacing and Electrophysiology Journal, pp. 126-133 (2006).
Schmieder, Ronald E., Renal denervation in patients with chronic kidney disease: current evidence and future perspectives, Nephrol. Dial. Transplant. gfac189 (2022).
Schneider, Peter A., Endovascular Skills, Quality Medical Publishing, Inc., 1998 ("Schneider").
Schneider, Peter, Endovascular Skills: Guidewire and Catheter Skills for Endovascular Surgery, 2nd ed., Marcel Dekker, Inc., New York, NY (2003).
Schuarte, Patrick et al., "Catheter Ablation of Cardiac Autonomic Nerves for Prevention of Vagal Atrial Fibrillation," Circulation vol. 102, p. 2774-2780, 2000.
Second Declaration of Chris Daft. Dated Jan. 10, 2023, in the Patent Trial and Appeal Board, United States Patent and Trademark Office, Petition No. PTAB-IPR2022-00431.
Selected documents from the File History of Inter Partes Reexamination 95/002110, exhibit to Petition for Inter Partes Review of U.S. Pat. No. 8,845,629, filed Jan. 13, 2022, in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No. 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000) ("Shonai 2000").
Slide deck from Medtronic Circulatory System Devices Panel Meeting, General Issues Panel: Clinical Evaluation of Anti-Hyperintensive Devices (Dec. 5, 2018).
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Smithwick, R. H., et al., "Splanchnicectomy for Essential Hypertension." J. Am. Med. Assoc., 152:1501-1504 (1953).
Stauffer, P.R. et al., "13 Interstitial Heating Technologies," Thermochemotherapy and Thermochemotherapy, p. 279-320, 1995.
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022, in the Patent Trial and Appeal Board, United States Patent and Trademark Office, Petition No. PTAB-IPR2022-00431.
Stipulation Modifying Schedule, dated Feb. 16, 2023, in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swanson, David K. et al., "Tissue temperature Feedback Control of Power, The Key to Successful Ablation," Innovations, vol. 6 No. 4, p. 276-282, Jul./Aug. 2011.
Swartz, John F. et al., Radiofrequency Endocardial Catheter Ablation of Accessory Atrioventricular Pathway Atrial Insertion Sites, 87 Circulation 487 (1993).
Tabei, Makoto et al., "A k-space method for coupled first-order acoustic propagation equations," J. Acoust. Soc. Am., vol. 111, No. 1, pt.1, p. 53-63, Jan. 2002.
Tanaka, Kazushi et al., "A New Radiofrequency Thermal Balloon Catheter for Pulmonary Vein Isolation," Journal of the American College of Cardiology vol. 38, No. 7, 2001.

(56) References Cited

OTHER PUBLICATIONS

Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07.012.
Teigen et al., Segmental Renal Artery Embolization for Treatment of Pediatric Renovascular Hypertension, J. Vasco Interv. Radiol. 3, 111-7 (1992).
Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of deposition of the Jan. 1, 2023 deposition of Dr. Robert Tucker.
Transcript of the Jan. 14, 2023 deposition of Dr. Daniel van der Weide.
Transcript of the Mar. 2, 2023 deposition of Dr. John Moriarty.
Transcript of the Mar. 3, 2023 deposition of Dr. Chris Daft.
Transcript of the Oct. 1, 2022 deposition of Dr. Farrell Mendelsohn.
Transcript of the Sep. 30, 2022 deposition of Dr. Chris Daft.
Trippodo, Nick C. et al., "Similarities of Genetic (Spontaneous) Hypertension," Circulation Research vol. 48, No. 3, p. 309-319, Mar. 1981.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Uchida, et al., "Effect of radiofrequency catheter ablation on parasympathetic denervation: A comparison of three different ablation sites." PACE, 21 :2517- 2521 (1998).
Ulmsten, Ulf et al., "The Safety and Efficacy of MenoTreat™, a new balloon device for thermal endometrial ablation," Acta Obstet Gynecol Scand 2001; 80: 52-57.
Umemura, Shin-ichiro, "Focused ultrasound transducer for thermal treatment," International Journal of Hyperthermia, vol. 31, No. 2, p. 216-221, 2015.
Urban, Bruce A. et al., "Three-dimensional Volume-rendered CT Angiography of the Renal Arteries and Veins: Normal Anatomy, Variants, and Clinical Applications," RG vol. 21 No. 2, p. 373-386, Mar.-Apr. 2001.
Vaezy, Shahram et al., "Image-Guided Acoustic Therapy", Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Wanchoo, Nishey, Medtronic Gets European and Australian Approval for Symplicity Spyral Multi-Electrode Renal Denervation Catheter, Medgadget (2013).
Wang, Shyh-Hau et al., "Effects of Low Intensity Ultrasound on the Conduction Property of Neural Tissues," IEEE International Ultrasonics, Ferroelectrics, and Frequency Control Joint $50^{th}$ Anniversary Conference, p. 1824-1827, 2004.
Weinstock, Marta et al., "Renal Denervation Prevents Sodium Retention and Hypertension in Salt-Sensitive Rabbits with Genetic Baroreflex Impairment", 90 Clinical Science 287 (1996).
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.
Wulff, V.J. et al., "Effects of Ultrasonic Vibrations on Nerve Tissues," P.S.E.B.M., vol. 76, p. 361-366, 1951.
Xu, J. et al, "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Yarmolenko, Pavel S. et al., "Thresholds for thermal damage to normal tissues: An update," Int. J. Hyperthermia, vol. 27 No. 4, p. 320-343, Jun. 2011.
Young, Robert R. et al., "Functional Effects of Focused Ultrasound on Mammalian Nerves," Science, vol. 134, p. 1521-1522, Nov. 1961.
Zazgornik, "Bilateral Nephrectomy: The Best, but Often Overlooked, Treatment for Refractory Hypertension in Hemodialysis Patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
Zimmer, J.E. et al., "The Feasibility of Using Ultrasound for Cardiac Ablation," IEEE Transactions on Biomedical Engineering, vol. 42, No. 9, p. 891-897, Sep. 1995.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.
U.S. Appl. No. 10/408,665, File History.
U.S. Appl. No. 11/532,814, Non-Final Office Action mailed Mar. 29, 2012.
U.S. Appl. No. 12/754,337, File History.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.
U.S. Appl. No. 14/683,966, Non-Final Office Action mailed Jun. 12, 2017, 14 pgs.
U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, Response filed Nov. 10, 2017 to Non-Final Office Action mailed Jun. 12, 2017, 13 pgs.
U.S. Appl. No. 15/204,349, Advisory Action mailed Jul. 9, 2019, 5 pgs.
U.S. Appl. No. 15/204,349, Final Office Action mailed Apr. 22, 2019, 16 pgs.
U.S. Appl. No. 15/204,349, Non-Final Office Action mailed Nov. 27, 2018, 14 pgs.
U.S. Appl. No. 15/204,349, Preliminary Amendment filed Nov. 30, 2016, 3 pgs.
U.S. Appl. No. 15/204,349, Response filed Feb. 27, 2019 to Non-Final Office Action mailed Nov. 27, 2018, 10 pgs.

(56) References Cited

OTHER PUBLICATIONS

U.S. Appl. No. 15/204,349, Response filed Jun. 24, 2019 to Final Office Action mailed Apr. 22, 2019, 12 pgs.
U.S. Appl. No. 15/204,349, Response filed Jun. 5, 2018 to Restriction Requirement mailed May 17, 2018, 7 pgs.
U.S. Appl. No. 15/204,349, Restriction Requirement mailed May 17, 2018, 7 pgs.
U.S. Appl. No. 15/261,732, Notice of Allowance dated Sep. 25, 2018.
U.S. Appl. No. 15/299,694, Advisory Action mailed Jul. 9, 2019, 5 pgs.
U.S. Appl. No. 15/299,694, Final Office Action mailed Apr. 22, 2019, 16 pgs.
U.S. Appl. No. 15/299,694, Non-Final Office Action mailed Nov. 27, 2018, 15 pgs.
U.S. Appl. No. 15/299,694, Response filed Feb. 27, 2019 to Non-Final Office Action mailed Nov. 27, 2018, 10 pgs.
U.S. Appl. No. 15/299,694, Response filed Jun. 24, 2019 to Final Office Action mailed Apr. 22, 2019, 11 pgs.
U.S. Appl. No. 15/299,694, Response filed Oct. 8, 2018 to Restriction Requirement mailed Aug. 6, 2018, 7 pgs.
U.S. Appl. No. 15/299,694, Restriction Requirement mailed Aug. 6, 2018, 6 pgs.
U.S. Appl. No. 15/943,354, Non-Final Office Action mailed Apr. 20, 2020, 7 pages.
U.S. Appl. No. 15/943,354, Non-Final Office Action mailed Jan. 13, 2020, 6 pages.
U.S. Appl. No. 15/943,354, Preliminary Amendment filed Apr. 3, 2018, 9 pgs.
U.S. Appl. No. 15/943,354, Response filed Dec. 19, 2019 to Restriction Requirement mailed Nov. 20, 2019, 8 pages.
U.S. Appl. No. 15/943,354, Restriction Requirement mailed Nov. 20, 2019, 8 pages.
U.S. Appl. No. 15/996,978, filed Jun. 4, 2018, Final Office Action dated Jun. 16, 2021.
U.S. Appl. No. 15/996,978, filed Jun. 4, 2018, Non-Final Office Action dated Sep. 2, 2021.
U.S. Appl. No. 15/996,978, filed Jun. 4, 2018, Notice of Allowance dated Oct. 6, 2021.
U.S. Appl. No. 15/996,978, filed Jun. 4, 2018, Response to Office Action dated Jul. 20, 2021.
U.S. Appl. No. 15/996,978, filed Jun. 4, 2018, Response to Office Action dated May 18, 2021.
U.S. Appl. No. 15/996,978, filed Jun. 4, 2018, Response to Office Action dated Sep. 22, 2021.
U.S. Appl. No. 15/996,978, filed Jun. 4, 2018, Final Office Action dated Feb. 19, 2021.
U.S. Appl. No. 15/996,978, Non-Final Office Action mailed Jun. 11, 2020, 8 pages.
U.S. Appl. No. 15/996,978, Preliminary Amendment filed Jun. 5, 2018, 11 pgs.
U.S. Appl. No. 15/996,978, Response filed Apr. 6, 2020 to Restriction Requirement mailed Feb. 7, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Restriction Requirement mailed Apr. 16, 2020, 8 pages.
U.S. Appl. No. 15/996,978, Restriction Requirement mailed Feb. 7, 2020, 7 pages.
U.S. Appl. No. 16/219,874, Final Office Action mailed Dec. 21, 2020, 7 pages.
U.S. Appl. No. 16/517,180, Preliminary Amendment filed Jul. 19, 2019, 12 pgs.
U.S. Appl. No. 17/453,636, filed Nov. 4, 2021, File History.
U.S. Pat. No. 10,039,901, File History.
U.S. Pat. No. 9,943,666, File History.
U.S. Pat. No. 9,981,108, File History.
U.S. Appl. No. 60/370,190, File History.
U.S. Appl. No. 60/415,575, File History.
U.S. Appl. No. 60/442,970, File History.
U.S. Appl. No. 60/616,254, File History.
U.S. Appl. No. 60/624,793, File History.
U.S. Appl. No. 60/747,137, File History.
U.S. Appl. No. 60/808,306, File History.
U.S. Appl. No. 60/816,999, File History.
U.S. Appl. No. 61/405,472, File History.

* cited by examiner

SYSTEMS AND METHODS FOR REAL-TIME TRACKING OF A TARGET TISSUE USING IMAGING BEFORE AND DURING THERAPY DELIVERY

CROSS-REFERENCE TO RELATED APPLICATIONS

This application is a continuation of U.S. patent application Ser. No. 17/171,940, filed Feb. 23, 2021; which in turn is a divisional of U.S. patent application Ser. No. 14/929,056, filed Oct. 30, 2015, now U.S. Pat. No. 10,925,579; which in turn claims priority to and the benefit of U.S. Provisional Patent Application No. 62/075,487, filed on Nov. 5, 2014, all of which are expressly incorporated by reference herein.

This application is related to international PCT patent application serial No. PCT/US2014/022141, titled "TRANSDUCERS, SYSTEMS, AND MANUFACTURING TECHNIQUES FOR FOCUSED ULTRASOUND THERAPIES", filed on Mar. 7, 2014, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the imaging field, and more specifically to a new and useful system and method for real-time tracking of a target tissue using imaging before and during therapy delivery.

BACKGROUND

Therapeutic energy delivery from a distance involves transmission of energy waves to affect a target tissue inside a patient's body. Therapeutic delivery of ultrasound waves has been used in a wide variety of therapeutic interventions, including lithotripsy, drug delivery, cancer therapy, thrombolysis, and tissue ablation. Non-invasive delivery of focused energy may allow for more efficient delivery of energy to the target tissue, improved cost effectiveness of treatment, minimized trauma to the patient's body, and improved recovery time.

Delivering energy over a distance requires targeting accuracy and technological flexibility while minimizing invasiveness into the patient. However, current methods fail to adequately track the target tissue motion while concurrently delivering the energy or therapy. A tissue in the body moves relative to the energy-delivering source from either the unintended patient body motion or the internal organs' motion due to heartbeat, breathing, blood flow, or other physiological functions. Current methods stop delivering the energy or therapy when the tissue moves out of focus or visibility due, at least, to breathing or shadows and reinitiates energy or therapy delivery when the tissue reemerges. The stopping and starting of therapy or energy delivery can have unintended consequences for the patient, such as variable dosing, uneven or insufficient therapy delivery to the target tissue, and prolonged procedure times.

Conventional ultrasound systems for tracking a targeted soft tissue motion have a much lower signal-to-noise ratio. Further, the shape of a target image can change more as it moves within the image because of ultrasound beam scan orientation, tissue deformation, ultrasound signal distortion and other factors. Controlling these factors is desirable for effective and accurate therapeutic energy delivering to the target tissue. Since soft tissue deforms at a macroscopic level, conventional tracking systems cannot adequately track such tissue deformation and motion. Further, tracking and energy delivery will halt when a conventional system loses the target tissue, due to, for example, rib shadows or deep breaths that move the target out of sight. This happens regularly in conventional systems. Conventional systems are not configured to deal with these motions, and even more importantly they are not configured to properly recover tracking once the image reappears, requiring user input to relocate the lost target tissue in the image.

Thus, there is a need for a new and useful system and method for tracking a target tissue using imaging before and during therapy delivery. In particular, there is a need for new and useful systems and methods configured to accommodate when tissue moves out of focus or visibility, and even more importantly configured to automatically recover tracking when the image reappears. This invention provides such a new and useful system and method.

SUMMARY

A system for identifying at least one anatomical structure and tracking a motion of the at least one anatomical structure using imaging before and during delivery of a therapy to a patient, includes: an imaging module configured to identify a location and a feature of a region of the anatomical structure in an image, wherein the imaging module comprises a tracker, a detector, and an integrator; and a therapy module comprising an ultrasound treatment transducer configured to deliver the therapy to a target tissue in the patient.

Optionally, the imaging module is configured to, in real-time, track the anatomical structure using a feature identification technique.

Optionally, the imaging module is configured to use a histogram of the anatomical structure in the image, or a feature matching technique.

Optionally, the imaging module is configured to identify a location of the target tissue to be treated by the therapy module.

Optionally, the tracker is configured to identify a new location or a new feature of the region of the anatomical structure in response to a change in the location and the feature of the region of the anatomical structure.

Optionally, the detector is configured to identify a shape, a location, and a feature of the region of the anatomical structure.

Optionally, the tracker, detector, and integrator are implemented in graphics processor unit (GPU), field-programmable gate array (FPGA) or digital signal processor (DSP) or any other units containing computation capabilities.

Optionally, the therapy module is configured to function concurrently with the imaging module.

Optionally, the therapy module is configured to deliver therapy to the target tissue despite a change in the location or the feature of the region of the anatomical structure.

Optionally, the anatomical structure comprises the target tissue.

Optionally, at least one of breathing, blood flow, conscious movement, or unconscious movement of the patient changes the location and/or the feature of the region of the anatomical structure.

Optionally, the imaging module is configured to identify the location and the feature of the region of the anatomical structure in less than 1 second.

Optionally, the imaging module is configured to identify the location and the feature of the region of the anatomical structure in less than 5 milliseconds.

Optionally, the target tissue comprises a renal artery.

Optionally, the ultrasound treatment transducer is configured to provide renal denervation.

Optionally, the imaging module is configured to track the region of the anatomical structure is using a B-mode image, Harmonic Imaging, or 3D ultrasound imaging.

Optionally, the imaging module is configured to track the region of the anatomical structure using a color Doppler image, a color power Doppler image, or a directional color power Doppler mode image.

Optionally, the system further includes a filter, wherein the filter is configured to reduce noise in the image, such that the imaging module can determine the location and the feature of the region of the anatomical structure in the image.

Optionally, the filter is configured to provide a filtered image that is visible to the tracker, the detector, or both the tracker and detector.

Optionally, the system further includes a user interface for allowing a user to choose between viewing the filtered image or an unfiltered image.

Optionally, the location is an x and y coordinate.

Optionally, the location is an x, y, and z coordinate.

Optionally, the image is an ultrasound image.

Optionally, the integrator is configured to integrate results from the tracker and detector and direct the therapy module to deliver the therapy to the target tissue.

Optionally, the location is in a plane.

Optionally, the location is in a three-dimensional space.

Optionally, a plane of movement of the anatomical structure is substantially parallel to an imaging plane of the imaging module.

Optionally, the feature includes one or more of a characteristic, intensity, density, contrast, and shape of the region of the anatomical structure.

Optionally, the imaging module and the therapy module are configured to function consecutively using an interleaving mechanism.

Optionally, the imaging module and the therapy module are configured to function concurrently using a continuous mechanism.

Optionally, the therapy module is configured to predict a future location or a future feature of the target tissue and to deliver the therapy to the target tissue when the target tissue reaches the future location or the future feature.

Optionally, the therapy module is configured to provide lithotripsy.

Optionally, the lithotripsy comprises treatment of a kidney stone, gallstone, bile duct stone, or ureter stone.

Optionally, the tracker comprises a short-term detector.

Optionally, the detector comprises a long-term detector.

A system for tracking a renal artery during delivery of an ultrasound therapy to a patient, includes: an imaging module configured to identify a location and a feature of a region of an anatomical structure in an ultrasound image, wherein the imaging module comprises a tracker, a detector, and an integrator; and a therapy module comprising an ultrasound treatment transducer configured to deliver the ultrasound therapy to the renal artery, wherein the ultrasound treatment transducer is configured to be mechanically moved and/or electronically controlled.

Optionally, the ultrasound treatment transducer is configured to be moved by a motion control mechanism to move the ultrasound treatment transducer.

Optionally, the ultrasound treatment transducer comprises a full circular annular phased array.

Optionally, the ultrasound treatment transducer comprises a partial circular annular phased array.

Optionally, the ultrasound treatment transducer is configured to be directed and moved to guide therapeutic energy to the renal artery.

Optionally, the ultrasound treatment transducer comprises a two-dimensional array and is configured to move therapy focus by a three-dimensional electronic control mechanism to guide therapeutic energy to the renal artery.

Optionally, the ultrasound treatment transducer is configured to be moved by a mechanical control mechanism to guide therapeutic energy to the renal artery.

A method for imaging during delivery of a therapy, includes: acquiring an image of a body portion of a patient; identifying a region of an anatomical structure that has a relationship to a target tissue in the image; tracking a location and/or a feature of the region of the anatomical structure in the image; integrating results from the act of tracking; generating a template library to cover possible changes of the location and/or changes of the feature of the region of the anatomical structure; and delivering the therapy to the target tissue while tracking the region of the anatomical structure in the image.

Optionally, the method further includes continuously delivering therapy to the target tissue despite a change in one or more locations and features of the region of the anatomical structure.

Optionally, the act of tracking occurs in response to a change in the location or the feature of the region of the anatomical structure.

Optionally, the region of the anatomical structure comprises the target tissue.

Optionally, at least one of breathing, blood flow, conscious movement, or unconscious movement of the patient changes the location and/or the feature of the region of the anatomical structure.

Optionally, the region of the anatomical structure is undetectable by the imaging module as a result of at least one of breathing, blood flow, conscious movement, and unconscious movement.

Optionally, the method further includes stopping imaging of the body portion of the patient when the region of the anatomical structure is undetectable.

Optionally, the method further includes automatically re-detecting the region of the anatomical structure location or feature.

Optionally, the automatically recovering step further comprises automatically recovering the region of the anatomical structure location or feature by first determining a last known location or feature of the region of the anatomical structure in the image.

Optionally, the act of tracking occurs in less than 5 milliseconds.

Optionally, the act of delivering the therapy comprises denervating renal nerves surrounding the renal artery.

Optionally, the act of delivering comprises delivering ultrasound to the target tissue.

Optionally, the act of tracking comprises using a B-mode image, Harmonic Imaging, or 3D ultrasound imaging.

Optionally, the act of tracking comprises using a color Doppler image, a color power Doppler image, or a directional color power Doppler mode image.

Optionally, the act of tracking comprises using an image in B-mode, Harmonic mode, color Doppler mode, color power Doppler mode, a combination of the B-mode, the Harmonic mode and the color Doppler mode.

Optionally, the method further includes filtering the image to obtain a filtered image, such that the anatomical structure can be tracked in the filtered image.

Optionally, the method further includes determining if a pre-existing template matches a result from the act of tracking.

Optionally, the method further includes determining if a result from the act of tracking should be updated as a new template.

Optionally, a position of the target tissue is based on the pre-existing template and a new template. For example, averaging (e.g., weighted averaging, non-weighted averaging) may be performed using information in the pre-existing template and the new template to determine the position of the target tissue.

Optionally, the method further includes generating a new template when a pre-existing template does not match a result from the act of tracking, wherein the new template defines or indicates a location and a shape of the target tissue.

A method for treatment includes: acquiring with an imaging module an image of a body portion of a patient; identifying a region of an anatomical structure that has a relationship to a target tissue in the image; tracking a location and/or a feature of the region of the anatomical structure in the image; transforming a target position of the target tissue from an imaging space associated with the imaging module to a treatment space associated with a therapy module through one or more position sensors and a transmitter; and delivering a therapy with the therapy module to the target tissue while tracking the region of the anatomical structure.

Optionally, the one or more position sensors and the transmitter are configured to link a position of an imaging transducer of the imaging module to a position of an ultrasound treatment transducer of the therapy module.

Optionally, the one or more position sensors comprises a magnetic sensor, an optical sensor, an ultrasound sensor, or a mechanical position sensor.

Optionally, the one or more position sensors are mounted on an imaging transducer of the imaging module.

Optionally, the transmitter is mounted on an imaging transducer of the imaging module.

Optionally, the one or more position sensors are mounted on an ultrasound treatment transducer of the therapy module.

Optionally, the transmitter is mounted on an ultrasound treatment transducer of the therapy module.

DETAILED DESCRIPTION

Figure 1:
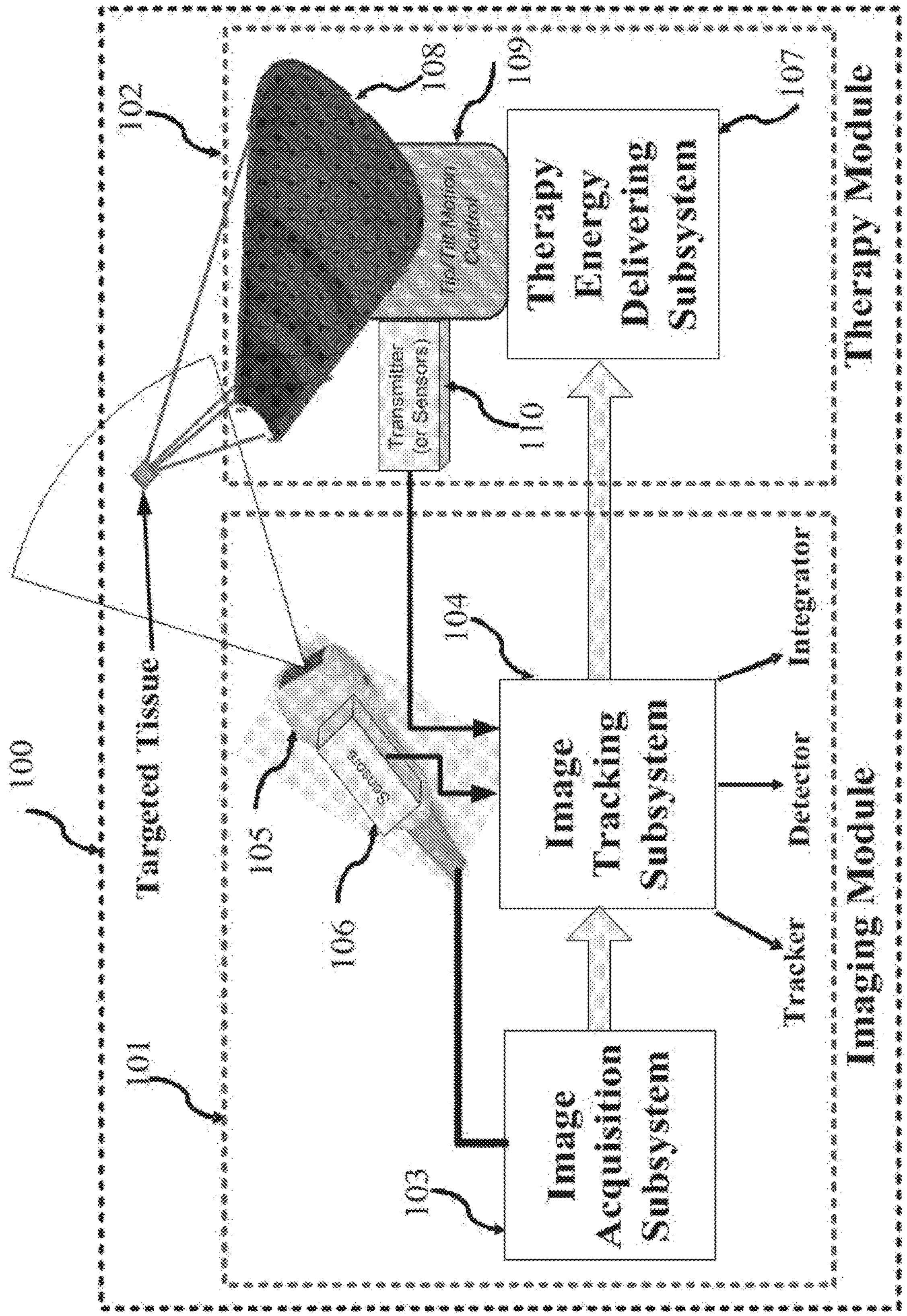
FIG. 1 illustrates a system for tracking a target tissue and delivering therapy to a target tissue, in accordance with a preferred embodiment.

The following description of the preferred embodiments of the invention is not intended to limit the invention to these preferred embodiments, but rather to enable any person skilled in the art to make and use this invention. Disclosed herein are systems and methods for identifying at least one anatomical structure and tracking the motion of the at least one anatomical structure using imaging before and during delivery of a therapy to a patient.

Described herein are systems and methods for tracking an anatomical structure in a patient and delivering therapy to an anatomical structure. The structure receiving the delivered therapy from the system is the target tissue. In some embodiments, the system may function completely non-invasively. Alternatively, the system may additionally include catheterization or otherwise surgically manipulating the patient. The system may be used to track an anatomical structure, such as an organ, blood vessel, artery, bone, blood, or any other type of anatomical structure. For example, in some embodiments, the system may function to track a kidney or renal artery of a patient. Alternatively, the system may be used to track a region of an anatomical structure, such as a curved edge or surface, a more distal or proximal portion of an organ, blood flow through a vessel, a distinguishing feature of an organ, for example glomeruli of the kidney, or any other region of interest of an anatomical structure. In some embodiments, a feature of an anatomical structure may be tracked, such as a location, shape, intensity, contrast, density, or otherwise characteristic of the anatomical structure. The location of an anatomical structure may include an x, y coordinate or an x, y, z coordinate. Alternatively, the location of the anatomical structure may be tracked in a two-dimensional plane or in three-dimensional space. The tracked anatomical structure may be a different structure than the anatomical structure receiving therapy from the system, such that a change in location or feature of the anatomical structure indicates a change in position of the target tissue. Alternatively, the anatomical structure may be the same as the target tissue, such that the target tissue is the anatomical structure that is being tracked. In some embodiments, the tracked anatomical structure may be a kidney and the target tissue receiving therapy may be a renal artery.

In some embodiments, the system may deliver therapy via ultrasound, mechanical vibrations, electromagnetic waves, lasers, X-ray or any other type of non-invasive radiation therapy. The therapy may include renal denervation, kidney stone disruption, gallstone disruption, bile duct stone disruption, ureter stone disruption, or any other type of non-invasive therapy.

In general, an anatomical structure may be lost and/or move during tracking and/or while receiving therapy. For example, an anatomical structure may be lost due to a shadow from another organ or bone structure, for example the rib cage. Alternatively or additionally, an anatomical structure may move due to breathing, blood flow, conscious movement, or unconscious movement of the patient during the procedure. In some instances, the region of the anatomical structure may become undetectable by the system as a result of breathing, blood flow, conscious movement, or unconscious movement of the patient. For example, an anatomical structure may move approximately 2 cm/second. In some instances, the anatomical structure may move substantially in a plane parallel to the plane of the system, or principal plane. Alternatively, the anatomical structure may move perpendicularly or variably relative to the system. As described herein, the system is configured to track a region of an anatomical structure despite shadows or deep breathing by a patient that moves an anatomical structure out of sight.

In some embodiments, the system may utilize an imaging module to locate the target tissue and track the position and/or movements of the target tissue, such that the therapy module can maintain its focus on the target tissue during the treatment process. In some embodiments, the imaging information may be used to confirm that the focus of the therapy module is properly positioned over the treatment region. The system then calculates the treatment parameter, such as dosing of ultrasound energy to be applied to the treatment region. For example the physician may enter the desired dosing level for a particular treatment. The system may also take into account other parameters, such as the distance of the target region from the therapy module, and calculate the appropriate ultrasound energy to apply to achieve the desired dosing at the target region. A particular treatment plan, such as a specific treatment pattern (e.g., energizing multiple spots within a treatment area), and a specific dosing routine (e.g., spreading a dose into multiple quantized delivery over a finite period of time to achieve the desired dose) may be selected. The system may then implement the treatment plan, and ultrasound energy may be delivered to the treatment region based on the treatment plan. In some embodiments, the treatment plan includes sequential lesions offset from the blood flow of a vessel and within 5 mm of one another. In another embodiment, the treatment plan includes sequential lesions offset from the blood flow and within 1 mm of each other. In another embodiment, the sequential lesions do not have an offset from one another and sequential lesions are applied atop one another in substantially the same position.

FIG. 1 illustrates a system 100 for tracking a region of an anatomical structure and delivering therapy to a target tissue, in accordance with a preferred embodiment. The system according to FIG. 1 preferably functions to image one or more anatomical structures, track a location or a feature of the anatomical structure, and delivery therapy to a target tissue. As shown in FIG. 1, a system 100 for identifying at least one anatomical structure and tracking the motion of the at least one anatomical structure using imaging before, during, or after delivery of a therapy to a patient includes an imaging module 101 and a therapy module 102. The imaging module 101 may be configured to acquire an image, identify one or more locations and/or features of an anatomical structure in the image, and/or track a location and/or feature of the anatomical structure within the image. The therapy module 102 of the system 100 may be configured to deliver therapy to a target tissue In some embodiments, the therapy module 102 may include a therapy energy delivering subsystem 107, which functions to generate controlled electrical energy to the ultrasound treatment transducer 108. In some embodiments, the ultrasound treatment transducer 108 transmits the ultrasound energy into the targeted tissue structure in a human body. In some embodiments, the ultrasound treatment transducer 108 may be a full circular annular phased array transmitting the focused ultrasound energy along the acoustic axis in depth direction into the targeted tissue structure in a human body. In other embodiments, the ultrasound treatment transducer 108 may be a section of full (e.g., partial) circular annular phased array transmitting the focused ultrasound energy along the acoustic axis in depth direction into the targeted tissue structure in a human body. For example, the transducer may have a pie shape so that the shape is less than a full circular shape. In some embodiments, the therapy module 102 may include a tip/tilt motion control unit 109 that adjusts the ultrasound treatment transducer rotation in tip and tilt directions to follow the targeted tissue motion. In other embodiments, the following of the targeted tissue motion may be accomplished by electronic control of the phasing of the ultrasound elements in the ultrasound treatment transducer, thereby obviating the need to mechanically move the ultrasound treatment transducer. In further embodiments, the control of the ultrasound energy focus may be accomplished using both electronic phasing control of ultrasound elements in the ultrasound transducer 108 and mechanical control of the movement of the ultrasound transducer 108 by the therapy module 102. In some cases, such technique may allow control of ultrasound energy focus at any position within a huge treatment volume in 3D space. In some embodiments, the therapy module 102 may further include a transmitter and/or one or more position sensors of a 3D position system 110.

In some embodiments, the imaging module 101 may include an image acquisition subsystem 103 that functions to acquire an image. In some embodiments, the image acquisition subsystem 103 may use ultrasound to acquire images of a region of an anatomical structure. In some embodiments, the imaging module 101 may further include an image tracking system 104 that functions to track a location and/or feature of an anatomical structure within the image acquired by the image acquisition subsystem 103. In some embodiments, the imaging module 101 may include an ultrasound imaging transducer 105 that transmits the ultrasound signals into the human body and receives the reflected signal from the tissue structures. In some embodiments, the imaging module 101 may further include position sensors 106 that are attached to the imaging transducer 105 to acquire the position of the imaging transducer 105 in 3D space and feed the position information to the imaging tracking subsystem 104. In some embodiments, the imaging transducer 105 may be linear, curved linear, phased, annular, or other types of imaging arrays that acquire an imaging plane inside a human body. In some embodiments, the imaging transducer 105 may be a two-dimensional array that acquires 3D ultrasound images inside a human body.

In some embodiments, the 3D position system determines the position of the ultrasound treatment transducer 108 and the relationship of the positions between the imaging transducer 105 and ultrasound treatment transducer 108. In some embodiments, an imaging ultrasound transducer 105 may be included near the therapy module 102, such that images may be acquired of the region of the anatomical structure being targeted, tracked, and treated as will be described below.

In some embodiments, the imaging module may acquire an ultrasound image. For example the imaging module may use echoes of ultrasound pulses to delineate objects or areas of different density in the body. A frequency range used may be between 0.5 to 18 megahertz or up to 50 or 100 megahertz. Alternatively, x-ray, computed tomography, magnetic resonance, or any other type of imaging modality, optical or otherwise, may be used. In some embodiments, the imaging of an anatomical structure may be acquired in a B-mode image, Harmonic image, a color Doppler image, a color power Doppler image, a directional color power Doppler mode image, any other type of image, or any combination of two or more of the foregoing. For example, in a B-mode image and/or Harmonic image, the system may image a two-dimensional cross-section of the tissue. Alternatively or additionally, the system may utilize color Doppler imaging, an imaging technique that combines anatomical information derived using ultrasonic pulse-echo techniques with velocity information derived using ultrasonic Doppler techniques to generate color-coded maps of tissue velocity superimposed on grey-scale images of tissue anatomy. Further, color power Doppler imaging has increased intensity and the added benefit of depicting flow in small vessels.

In some embodiments, the imaging module 101 may function to identify a position of a region of an anatomical structure, such that the therapy module 102 may deliver therapy in a substantially continuous manner to the target tissue. The imaging module 101 may rapidly identify the position of the target tissue such that the therapy module 102 may then rapidly deliver therapy to the target tissue. In an interleaving pattern, the position may be identified, followed by therapy delivery, followed by position identification, and so on. This interleaving pattern of the imaging module and therapy module may occur in rapid, repetitive succession such that therapy is delivered substantially continuously. The rapid, repetitive succession is required, such that the target tissue may be tracked substantially continuously and the therapy may be delivered substantially continuously.

In some embodiments, the imaging module 101 may function rapidly, such that a dose of therapy may be delivered substantially continuously to the target tissue without significant delay between identifying a position of the target tissue and delivering therapy to the target tissue or between subsequent doses of therapy to the target tissue. For example, the imaging module 101 may identify one or more locations and/or features of the region of the anatomical structure in less than 10 seconds, 5 seconds, 3 seconds, 2 seconds, or 1 second. Alternatively, the imaging module may identify one or more locations and/or features of the region of the anatomical structure in less than 1000 milliseconds, 750 milliseconds, 500 milliseconds, 250 milliseconds, 100 milliseconds, 75 milliseconds, 50 milliseconds, 25 milliseconds, 10 milliseconds, 5 milliseconds, or 1 millisecond. In some embodiments, the imaging module may use a frame rate of greater than or equal to 20 Hz. Alternatively, the imaging module may use a frame rate of less than 20 Hz.

Returning to FIG. 1, in some embodiments, the image tracking subsystem 104 of imaging module 101 includes a tracker and a detector. Both the tracker and detector are computer algorithms configured to identify and track a shape, location, and/or feature of a region of an anatomical structure in an image by searching within a region of interest in the image for a shape, location, and/or feature of the region of the anatomical structure. As described below in further detail, the imaging module 101 may weigh results from the tracker and detector differentially, such that in some instances only the tracker results may be used or, alternatively, only the detector results or both. In some embodiments, the tracker and detector may each independently identify and track a shape, location, and/or feature of a region of an anatomical structure in an image. The tracker and detector may identify motion of a region of an anatomical structure and compensate for the motion by adjusting the focal point, such that therapy may be delivered substantially continuously to a target tissue. In some embodiments, a system may use both a tracker and detector to identify and track a region of an anatomical structure in an ultrasound image. The tracker and the detector complement each other, increase robustness of the system, and compensate for non-uniformity of ultrasound waves (as compared to imaging with light) in their interactions with an object or tissue being imaged.

In some embodiments, the tracking capabilities of the tracker and detector may be combined into one algorithm, negating the need for a separate tracker and detector. In some embodiments, results from the tracker and detector may be compared to templates, which identify a previous shape, location, and/or feature of the region of the anatomical structure. For example, the tracker may be a short-term detector in that the results are compared to several previous image ($I_{n-p}$, $I_{n-p-1}$ - - - $I_{n-3}$, $I_{n-2}$, $I_{n-1}$) and use weighted function to obtain the final position. In some embodiments, the tracker will first look for change near the previous location (i.e. previous image ($I_{n-1}$)) rather than looking throughout the entire image. Further for example, the detector may be a long-term detector in that the results are compared to more than one template (i.e. a template pool) from any number of previous images. In some embodiments, the long-term template management samples breathing cycles. In general, the combination of the complimentary tracker and detector will enable the system to compensate automatically, without user intervention, if the target becomes lost or unfocused. Alternatively, any quantity and/or type of trackers and/or detectors may be used. In some embodiments, the system may include additional trackers and/or detectors such that the additional trackers and/or detectors complement the existing trackers and detectors for tracking a region of an anatomical structure. In some embodiments, the multiple complementary trackers and/or detectors may lead to an increased computation time and/or memory requirements, however the robustness of the system will also improve. In some embodiments, the system 100 further includes an integrator. The integrator is an algorithm configured to compare and/or integrate the results from tracker and detector of the image tracking subsystem of the imaging module 101 and direct the therapy module 102 to deliver the therapy to the target tissue.

Figure 2:
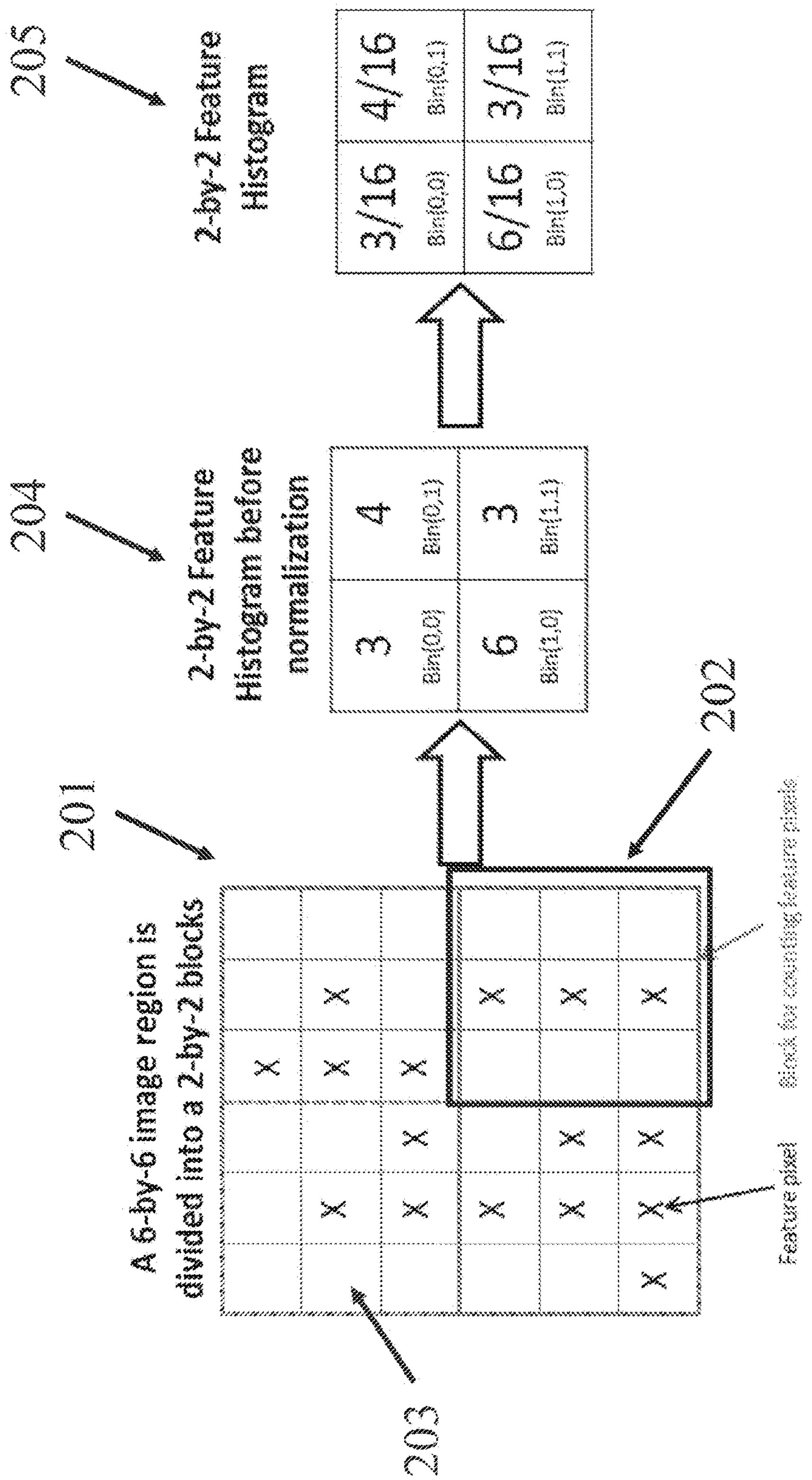
FIG. 2 illustrates a tracking algorithm, in accordance with a preferred embodiment.

The tracker and detector are algorithms for determining a location and/or feature of a region of an anatomical structure. In some embodiments, as shown in FIG. 2, a feature histogram algorithm may be used. Feature histogram describes the two-dimensional spatial distribution of the featured pixels in a defined area or analysis region 201. As shown in FIG. 2, the analysis region 201 may be equally divided into several smaller regions. The analysis region 201 containing 6 by 6 pixels, as shown in FIG. 2, is subdivided into 4 sub-regions 202, which contains 3 by 3 pixels 203. However, it should be understood that any number of pixels in analysis region 201 may be used, for example less than 36 pixels or more than 36 pixels. For example, a 5×5, 75×75, 100×100, 500×500, or 1000×1000 pixels, or anything above, below or in-between may be utilized.

In some embodiments, as shown in FIG. 2, a pixel 203 of an anatomical structure may be identified, for example by contrast, pixel density, or intensity, in the analysis region 201, denoted by an "x" in the pixel 203. Each "x" or pixel feature may be totaled for each sub-region, resulting in a 2 by 2 feature histogram 204 of region 201. The 2 by 2 feature histogram 204 is further normalized into a 2 by 2-normalized feature histogram 205. The distribution of the feature histograms indicates a location or feature of the region of the anatomical structure. However, it should be understood that any number of histogram dimension can be used, for example 4 by 4, 8 by 8, 8 by 4, 4 by 8, 16 by 16, 16 by 8, 8 by 16, 32 by 32 or any other number.

In some embodiments, a first feature histogram indicating a first location or feature of a region of an anatomical structure may be compared to second feature histogram indicating a second location or feature of the region of the anatomical structure. In some embodiments, the first or second feature histogram may include a template from a previous image. The two histograms may be compared using equation (1) below, where $H_1^{ij}$ is the first feature histogram, $H_2^{ij}$ is the second feature histogram, N is the total number of bins in the x-direction of the 2D feature histogram, M is the total number of bins in the y-direction of the 2D feature histogram, and D is the distance between the two histograms between 0 and 1. When D=0, the two histograms are identical. Conversely, when D=1, the two histograms are the most different.

$$D = \sqrt{1 - \sum_{i=1}^{N}\sum_{j=1}^{M}\sqrt{H_1^{ij}H_2^{ij}}} \quad (1)$$

In some embodiments, alternative algorithms may be employed, such as sum squared difference, sum absolute difference, or normalized cross correlation (NCC). For example, in NCC, a position of the region of the anatomical structure is determined by a pixel-wise comparison of the current image with the template containing a previous position of the region of the anatomical structure. The search region in the template is shifted in discrete steps in the N and M directions, and then the comparison is calculated (i.e. subtracting the mean and dividing by the standard deviation at every step) over the template search area for each position. The position of the maximum NCC values indicates the position of the region of the anatomical structure in the current image. Alternatively, any other threshold NCC value (i.e. minimum) may be used.

Figure 3A:
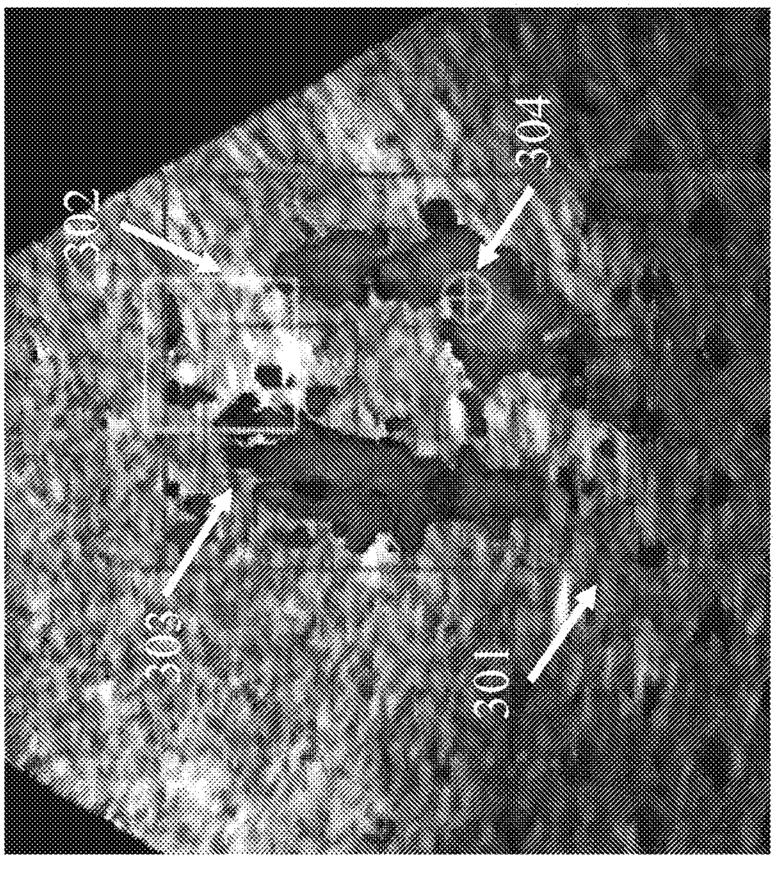
FIGS. 3A and 3B illustrate images used for tracking and delivery of therapy to a target tissue, in accordance with a preferred embodiment.
Figure 3B:
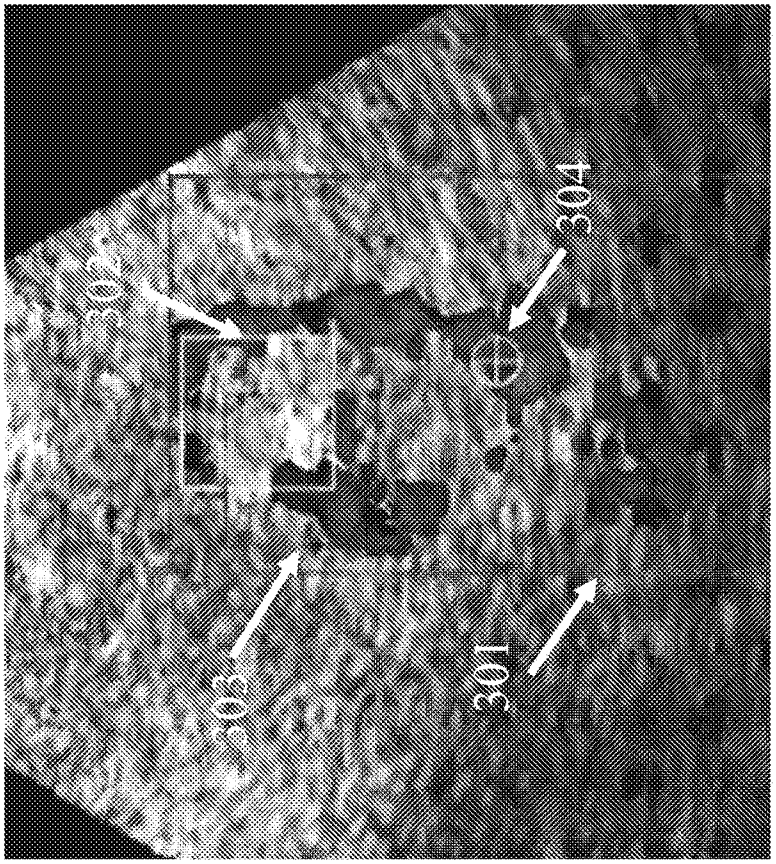

FIGS. 3A and 3B illustrate a region of an anatomical structure that is being tracked by two tracking boxes 302, 303 working on different tissue areas, in and around a region 301 that is viewable by a user. Each tracking box is associated with its own tracker, detector, and integrator. As shown in FIG. 3, two tracking boxes 302, 303 are used to increase the robustness and fidelity of the system, such that both the first and second tracking boxes are tracking a similar region of the anatomical structure in each of the tracking boxes 302, 303. Tracking is not completely lost and therapy is not stopped unless both boxes lose tracking. For example, if the first tracking box (associated with tracker, detector, and integrator) becomes lost and/or is unable to find the region of the anatomical structure, the second tracking box (associated with tracker, detector, and integrator) will continue tracking the region of the anatomical structure and therapy delivery will continue and vice versa.

In this example, the tracking boxes are tracking a location or feature of a region of an anatomical structure in two images, at opposite ends of a breathing cycle, using a feature histogram algorithm, as described above. For example, a beginning of a breathing cycle is shown in FIG. 3A and an end of a breathing cycle is shown in FIG. 3B. The crosshairs 304 indicate a target region or tissue for receiving therapy. As shown in FIG. 3, the target tissue (e.g. renal artery) receiving therapy is distinct from the regions of the anatomical structure (e.g. tissue) that is being tracked by the tracking boxes. In some embodiments, the search region may be any size, for example 361 pixels by 420 pixels. Alternatively, the search region may be larger than 361 pixels by 420 pixels or less than 361 pixels by 420 pixels. The tracking boxes 302, 303 may be any size, for example 64×64 pixels. Alternatively, the tracking boxes may be less than 64×64 pixels or greater than 64×64 pixels. In some embodiments, a user may select the tracking box size. Alternatively, the tracking box size may be selected automatically by the system.

Alternatively, only one tracking box or more than two tracking boxes may be used. In some embodiments, the system may include additional tracking boxes to add redundancy to the system. In some embodiments, the multiple complementary trackers and/or detectors may lead to an increased computation time and/or memory requirements, however the robustness of the system will also improve.

In some embodiments, the tracking performed by the first and second tracking boxes may occur with an accuracy of root-mean-square (RMS) error of less than or equal to 2 mm. Alternatively, the RMS error may be more than 2 mm, but still within a suitable accuracy. In some embodiments where two tracking boxes are used, if both the tracking boxes 302, 303 are lost, the tracking boxes 302, 303 may recover at the same time and maintain the same relative position with error within less than or equal to 40 pixels. Alternatively, the error may be within more than 40 pixels. Further, in some embodiments, if the region of the anatomical structure moves outside of the image, the tracker and detector will cease to track the region of the anatomical structure.

Figure 4:
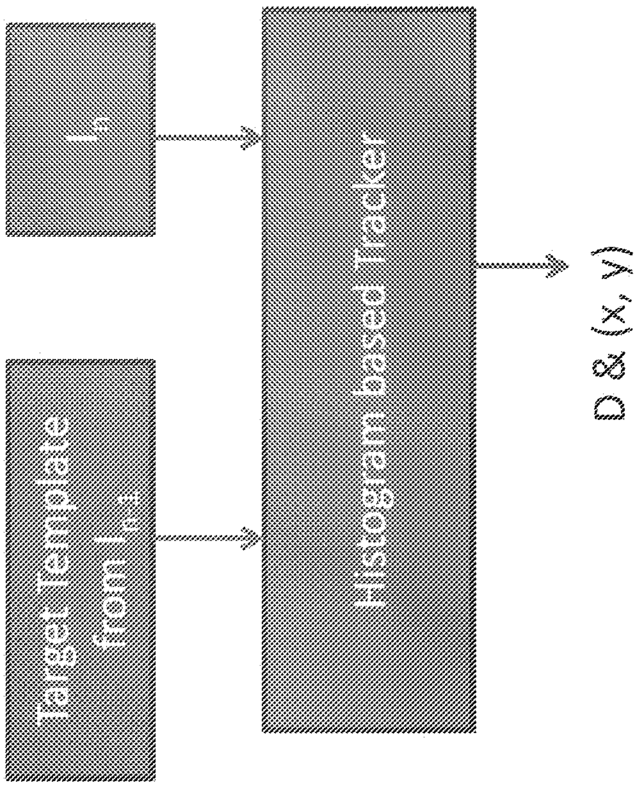
FIG. 4 illustrates a flow chart for the functioning of a tracker, in accordance with a preferred embodiment.

In some embodiments, as shown in FIG. 4, a tracker may function as a short-term detector, as described above. The tracker may compare a feature histogram of a current location or feature of a region of an anatomical structure in a current image ($I_n$) to a template. In some embodiments, the template may be a feature histogram of a previous location or feature of the region of the anatomical structure in a previous image ($I_{n-1}$). In some embodiments, the tracker may search for a change in a region of the anatomical structure near a previous location of the region of the anatomical structure in the template instead of searching an entire template. The two feature histograms are compared, for example using equation (1), and the minimum distance D between the two feature histograms may be determined and the x, y coordinates of the point of the minimum distance D may be identified, as shown in FIG. 4. Alternatively, a maximum distance D or any other threshold may be used when comparing two or more feature histograms.

Figure 5:
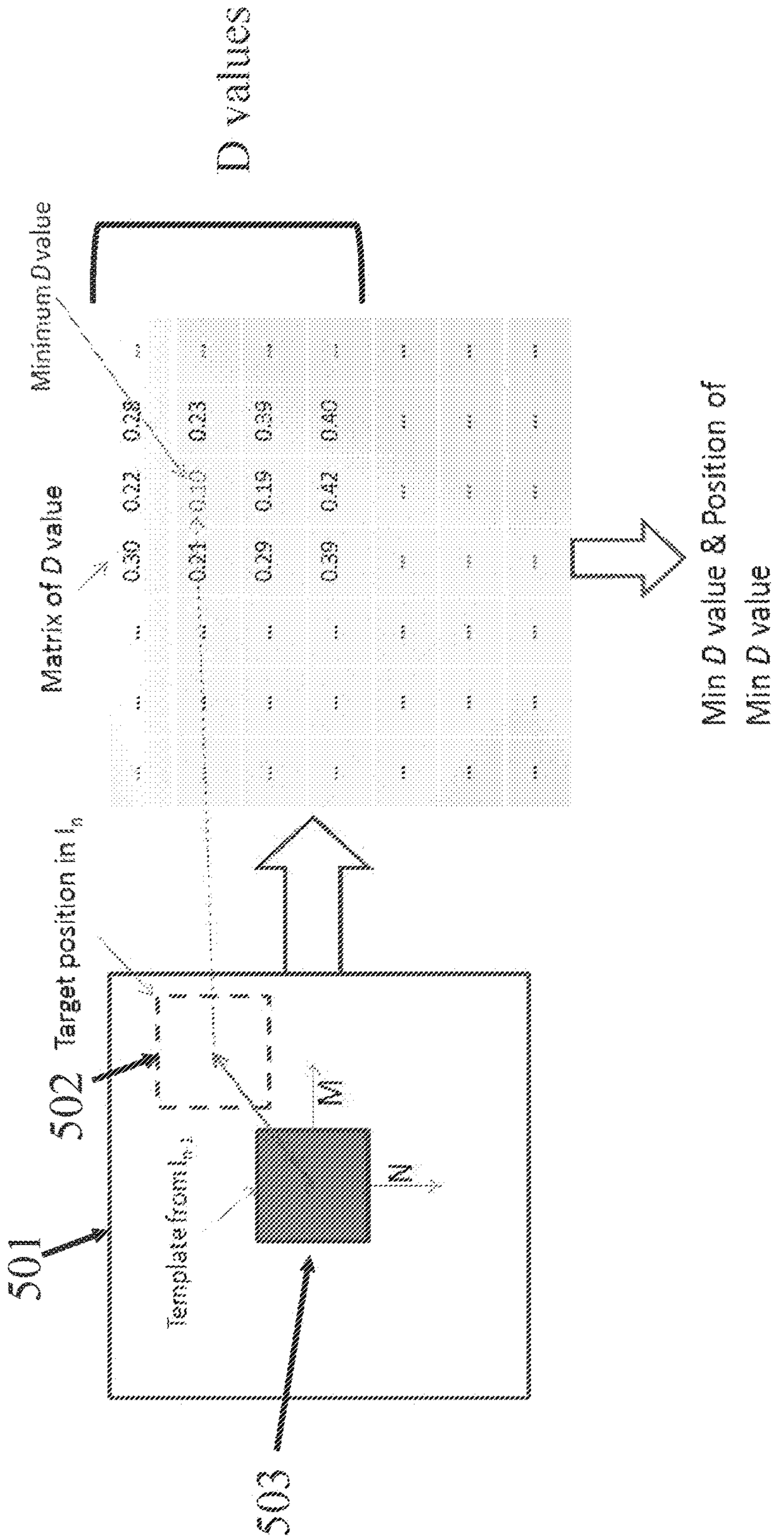
FIG. 5 illustrates a tracker algorithm, in accordance with a preferred embodiment.

As shown in FIG. 5, within the search region 501, the tracker tracks a possible current location or feature 502 of a region of the anatomical structure in the current image ($I_n$). The previous location or feature (with M, N coordinates) of the region of the anatomical structure from image ($I_{n-1}$) is a template 503, as described above. In some embodiments, the tracker may search for a change in a region of the anatomical structure near a previous location of the region of the anatomical structure instead of searching the entire image. The distance between the feature histograms of the possible current location or feature 502 and the previous location or feature 503 of the region of the anatomical structure is calculated. Each of the distances may be represented by value D, such that the minimum D value and the position of the minimum D value indicate a best match between a current location or feature and a previous location or feature of the region of the anatomical structure in the template.

Figure 6:
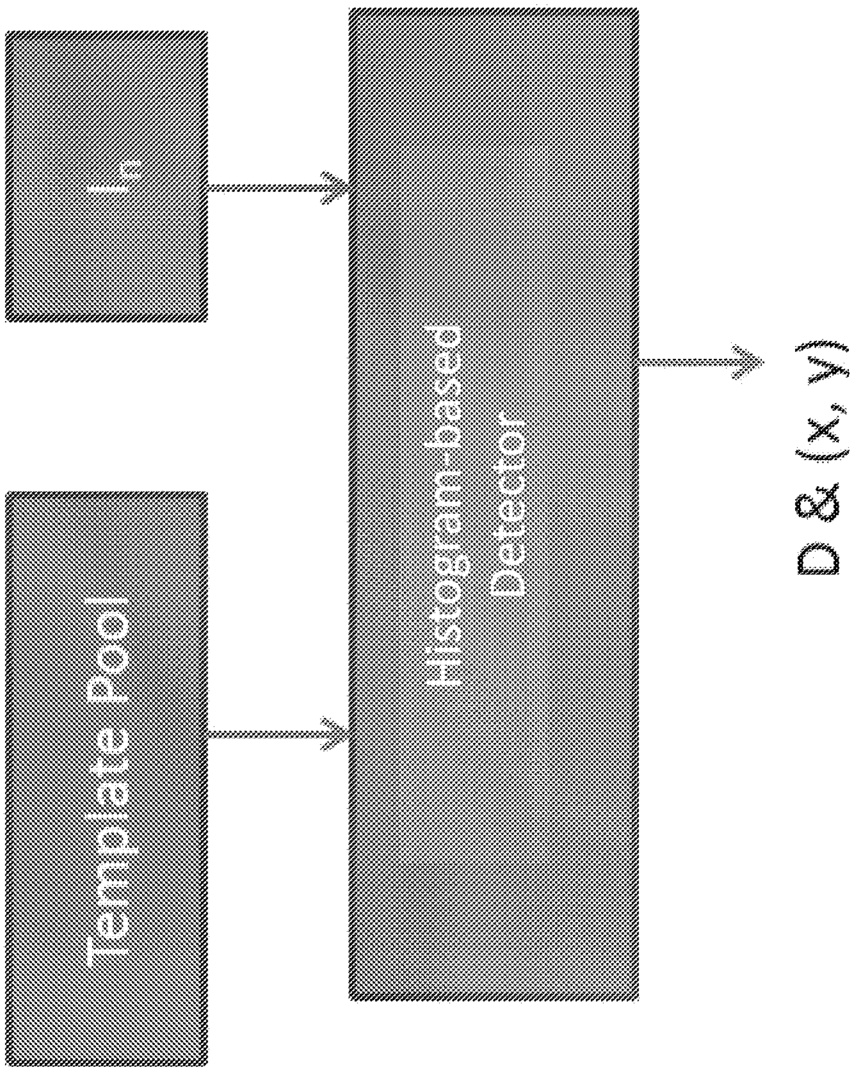
FIG. 6 illustrates a flow chart for the functioning of a detector, in accordance with a preferred embodiment.
Figure 7:
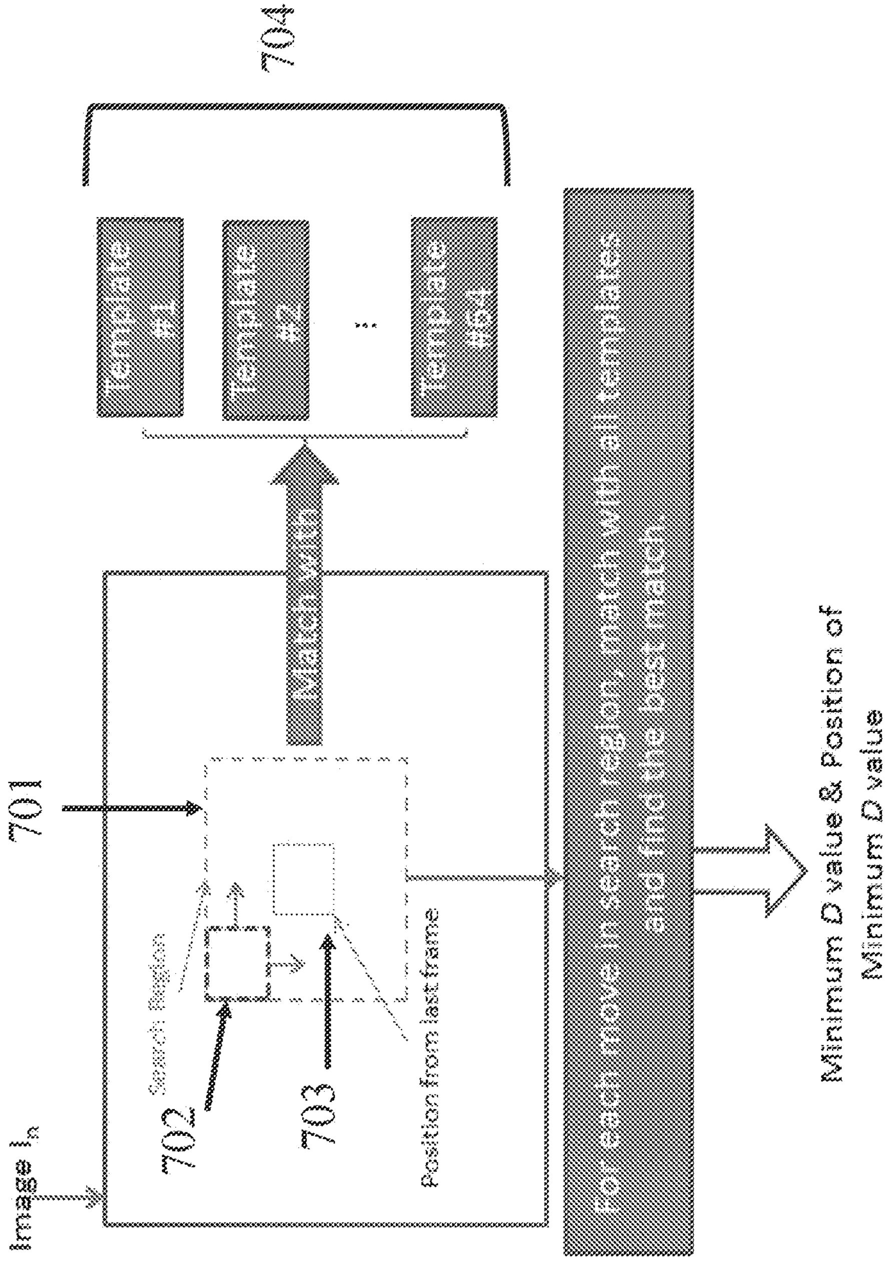
FIG. 7 illustrates a detector algorithm, in accordance with a preferred embodiment.

As shown in FIGS. 6 and 7, within the search region 701, the detector may function as a long-term detector, as described above. The detector may detect a possible current location or feature of a region of the anatomical structure in a current image ($I_n$). The feature histogram of the possible current location or feature 702 in a current image $I_n$ is compared to a template pool 704 comprising feature histograms for one or more templates of previous locations and/or features, for example 703, of the region of the anatomical structure in previous images ($I_{n-1}$). For example, a template pool 704 may include a plurality of templates. As one example, the template pool 704 may include 64 templates. The feature histograms of the possible current location or feature 702 of a region of the anatomical structure are compared to the feature histograms of the one or more templates, for example 703, through calculating the D value. The template corresponding to the minimum D value and the position of the minimum D value indicates a best match between a current location or feature 702 and the template from the template pool 704, identifying the location or feature as the region of the anatomical structure 701, as shown in FIG. 7. In some embodiments, a maximum Normalized Cross Correlation (NCC) value may correspond to a best match between a current location or feature and the template from the template pool, which could replace the D value as described above.

In some embodiments, the feature histogram of the current image is compared to all templates in the template pool. Alternatively, the feature histogram of the current image may be compared to a subset of the template pool. In some embodiments, all templates search in their own search regions and the region of the anatomical structure is at the position, which gives the maximum (i.e. NCC value) or minimum value (i.e. sum squared difference value) in all search regions of the templates.

Figure 8:
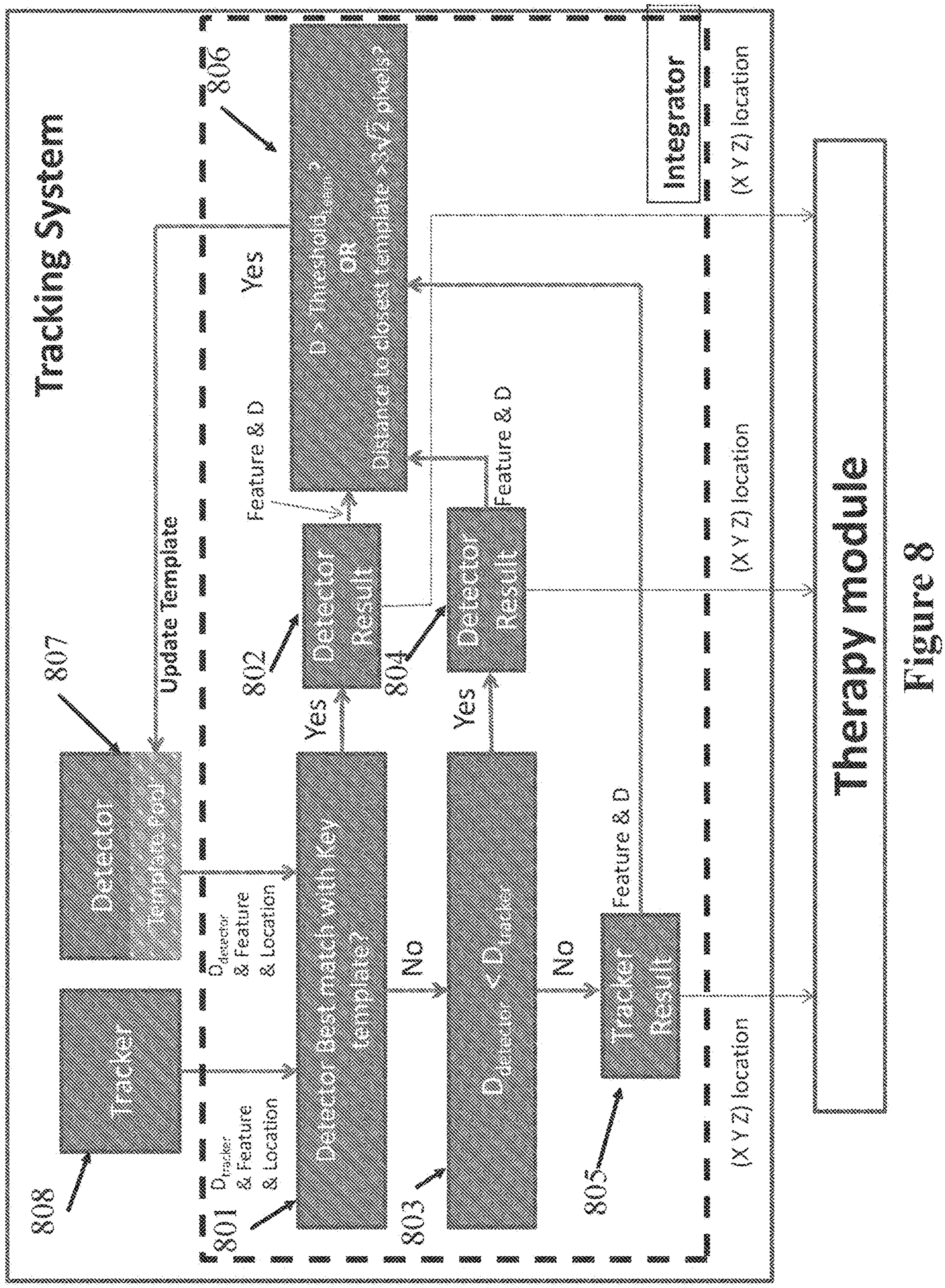
FIG. 8 illustrates a flow chart for the functioning of an integrator, in accordance with a preferred embodiment.

FIG. 8 illustrates an integrator flow chart. In some embodiments, as shown in FIG. 8, an integrator is an algorithm that compares the tracking results from the tracker and detector and determines (1) if the results from the tracker or detector should be used in determining a current location or feature of the region of the anatomical structure and (2) if the results from the tracker and detector should be added as a template to the template pool. In some embodiments, the integrator weighs the results of the detector more heavily. As shown in FIG. 8, if the results from the detector match with a key template, which is a template sampled throughout the motion cycles, then the integrator will use the detector results 802. Otherwise, if the distance value D determined by the detector is less than the distance value D determined by the tracker 803, the integrator will use the results from the detector 804, such that the smaller distance value D from the detector more accurately defines the feature histogram of the location or feature. Alternatively, if the distance value D determined by the detector is more than the distance value D determine by the tracker, then the integrator further evaluates the results from the tracker 805. If the distance value D is greater than a predetermined threshold or if the distance of the current location to the closest template location is greater than a predefined pixel distance (L), for example $3\sqrt{2}$ or any other distance, the feature histogram denoted by distance value D will be updated as a template and maintained as part of the template pool 807. In some embodiments, if the location of a current feature is a predefined distance (L) from all other templates in the pool, then the current feature will be saved as a "key" template. Any of the above integrations performed by the integrator may be sent to the therapy module, such that an x, y, z coordinate of the current location may be sent to the therapy module and the therapy module may deliver therapy to the target tissue, as shown in FIG. 8. In some embodiments, the time between the therapy module receiving instructions and delivering therapy is less than or equal to 50, 40, 30, 20, 10, 5, or 1 milliseconds. Alternatively, the time between receiving instructions and delivering therapy may be more than 50 milliseconds.

Figure 9A:
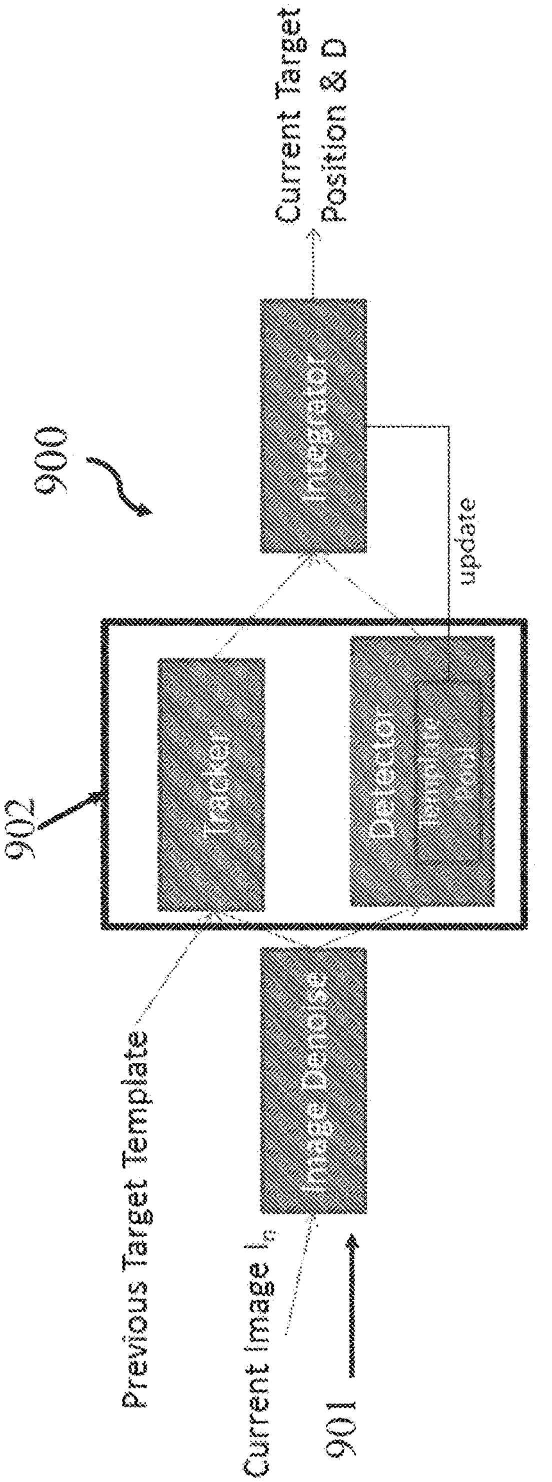
FIGS. 9A and 9B illustrate a system including a filter for tracking a target tissue and delivering therapy to a target tissue, in accordance with a preferred embodiment.

In some embodiments, as shown in FIG. 9A, a system 900 for tracking a region of an anatomical structure and delivering therapy to a target tissue may further include a filter 901. The filter may use an algorithm to reduce noise in the image ($I_n$), such that the imaging module 902 may determine one or more locations and/or features of the region of the anatomical structure in the image ($I_n$). In some embodiments, the noise may include speckle, multiple coherent reflections from the environment surrounding the region of the anatomical structure or target tissue, or any other type of noise. In some embodiments, the filtered image may be visible only to one of the tracker or detector. Alternatively, both the tracker and detector may use the filtered image. In some embodiments, a user of the system 900 may select between viewing the filtered image or an unfiltered image.

Figure 9B:
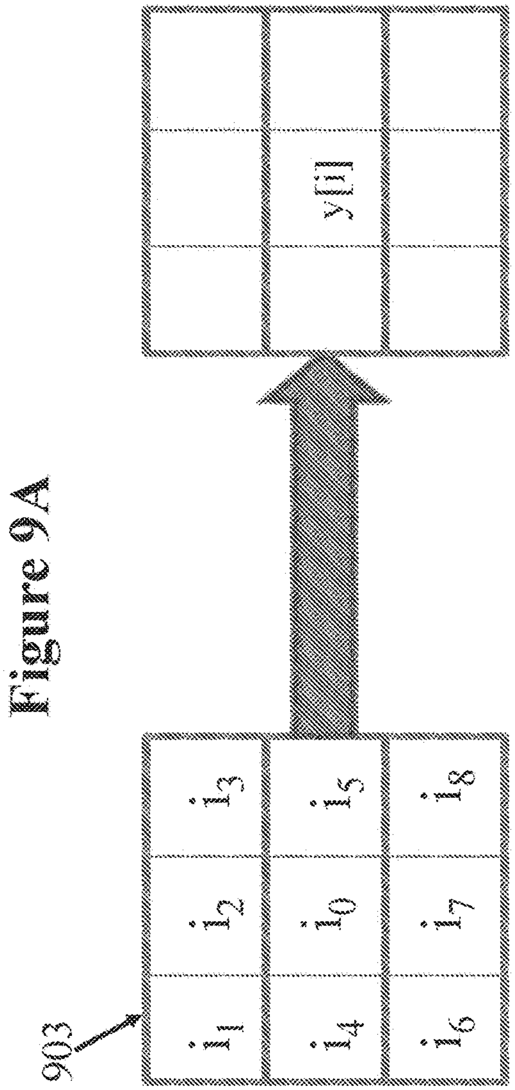

In some embodiments, as shown in FIG. 9B, a filter may use a simple moving average filter to remove noise in an image ($I_n$). As shown in FIG. 9B, each region 903 of the image may be identified ($i_n$) and the average intensity of the pixels in each region may be determined. Equation (2) may be used to smooth the image, such that y[i] equals the smoothed pixel intensity, M equals the number of regions 903 in the average, i equals the location of smoothed pixel, and j equals the index within the region. Alternatively, any other type of filtering equation may be used.

$$y[i] = \frac{1}{M}\sum_{j=0}^{M-1} x[i*j] \qquad (2)$$

Figure 10:
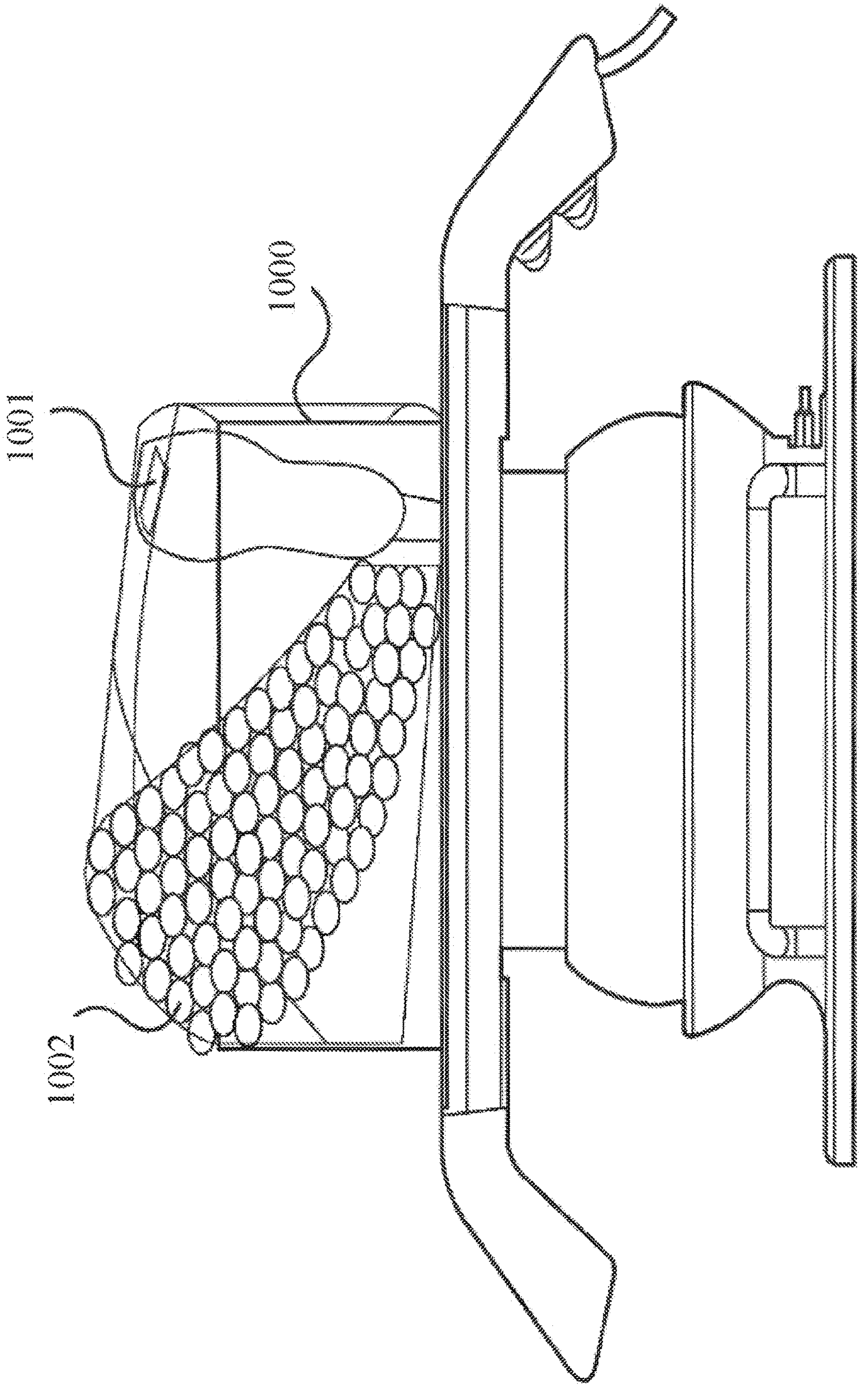
FIG. 10 illustrates a therapy module, in accordance with a preferred embodiment.
Figure 11:
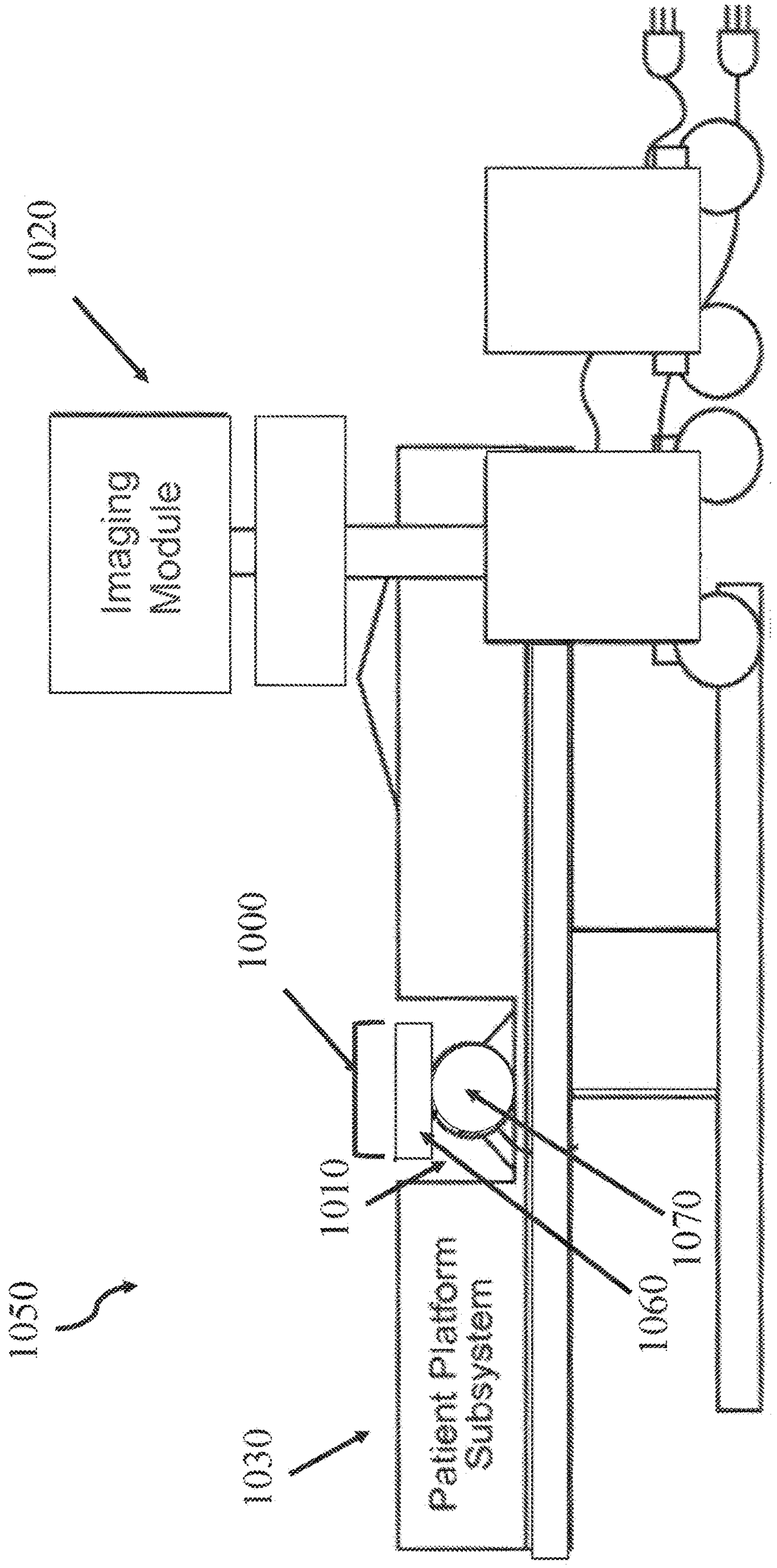
FIG. 11 illustrates a system including an imaging and therapy module, in accordance with a preferred embodiment.

In some embodiments, where the integrator integrated the results from the tracker and detector, as described above with respect to FIG. 8, the therapy module may receive a current target tissue location and a distance to the current target tissue location from the integrator. In some embodiments, the therapy module 1000 may include one or more ultrasound transducers 1001, 1002, as shown in FIG. 10. The therapy module 1000 may include a phased or fixed array of ultrasound transducers 1002 for delivering therapy to the target tissue. Further, in some embodiments, as shown in FIG. 10, the therapy module may include a second phased or fixed array of ultrasound transducers 1001 for acquiring images of the region of the anatomical structure. The region of the anatomical structure may then be tracked in the image by the tracker and detector, as described above. As shown in FIG. 11, the therapy module 1000 may be integrated into a patient platform 1030, such that the therapy module 1000 is positioned in a cavity 1010 of the patient platform 1030 while maintaining access to a patient lying on the patient platform 1030. In some embodiments, the imaging module 1020 may be in the same room and/or electrically connected to the patient platform 1030 and/or the therapy module 1000. Alternatively, the imaging module 1020 may be in communication with the therapy module 1000 through Bluetooth, Wi-Fi, or any other type of connection. Other features and aspects of the system 1050 of FIG. 11 are disclosed in PCT Application Serial Number 2014/022141, which is herein incorporated by reference.

In some embodiments, the ultrasound transducer of the therapy module may be moved, repositioned, or otherwise relocated by a motion control mechanism. Alternatively, the ultrasound transducer of the therapy module may be directed and moved to guide therapeutic energy to the target tissue, for example by an applicator 1060. In some embodiments, the ultrasound transducer of the therapy module may be moved by a three-dimensional electronic beam steering control mechanism to guide therapeutic energy to the target tissue. Alternatively, the ultrasound transducer of the therapy module may be moved by a mechanical control mechanism to guide therapeutic energy to the target tissue.

Figure 12A:
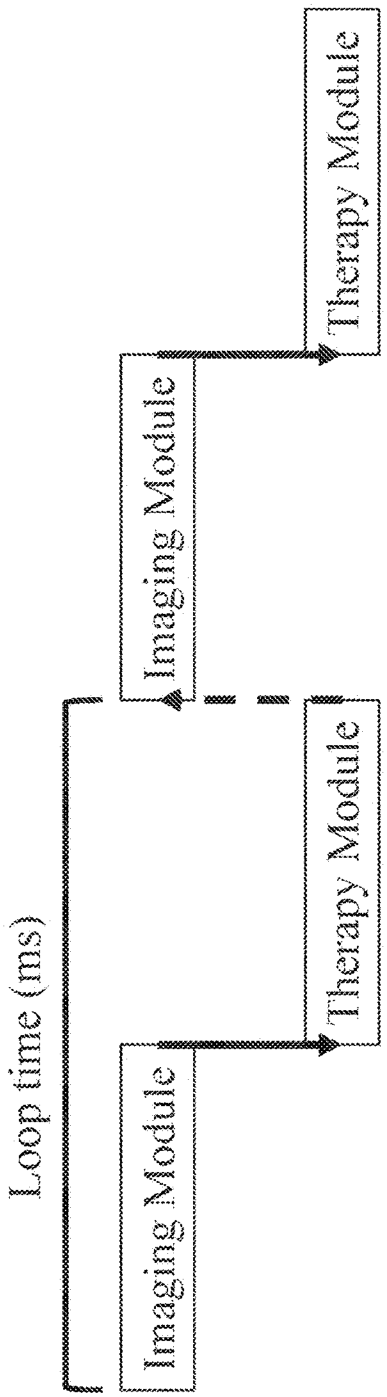
FIGS. 12A and 12B illustrate an interleaving and a continuous mechanism for imaging and therapy delivery, respectively, in accordance with first and second preferred embodiments.
Figure 12B:
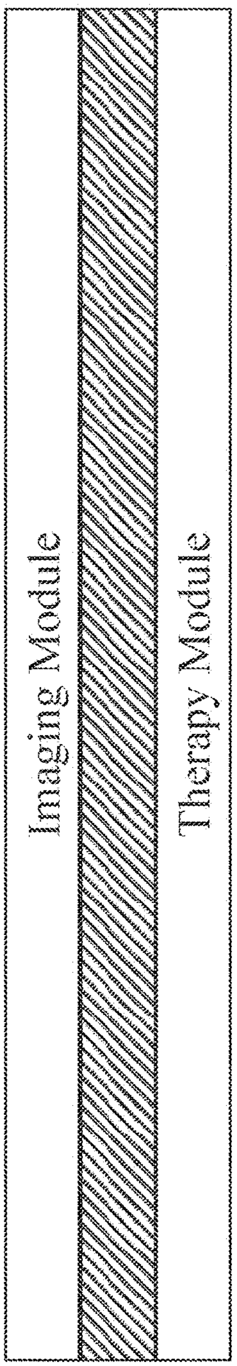

In some embodiments, as shown in FIG. 12A, the imaging module and therapy module may function in rapid succession in an interleaving mechanism. FIG. 12A illustrates the interleaving pattern with solid arrows representing hard sync triggers and dashed arrows representing soft sync triggers. The interleaving pattern, as shown in FIG. 12A, may continue until the prescribed dose of therapy has been delivered. In some embodiments, the therapy module will be re-targeted to a new lesion or position and the interleaving mechanism will resume. Alternatively, in some embodiments, the imaging module and therapy module may function simultaneously, such that therapy is continuously being delivered while the imaging module is transmitting tracker and detector results to the therapy module, as shown in FIG. 12B. Alternatively or additionally, the therapy module may function using a predictive mechanism, such that the therapy module may predict a future position of the region of the anatomical structure that is being tracked by the imaging module from several previous target positions and move to that predicated position to deliver therapy.

Figure 13:
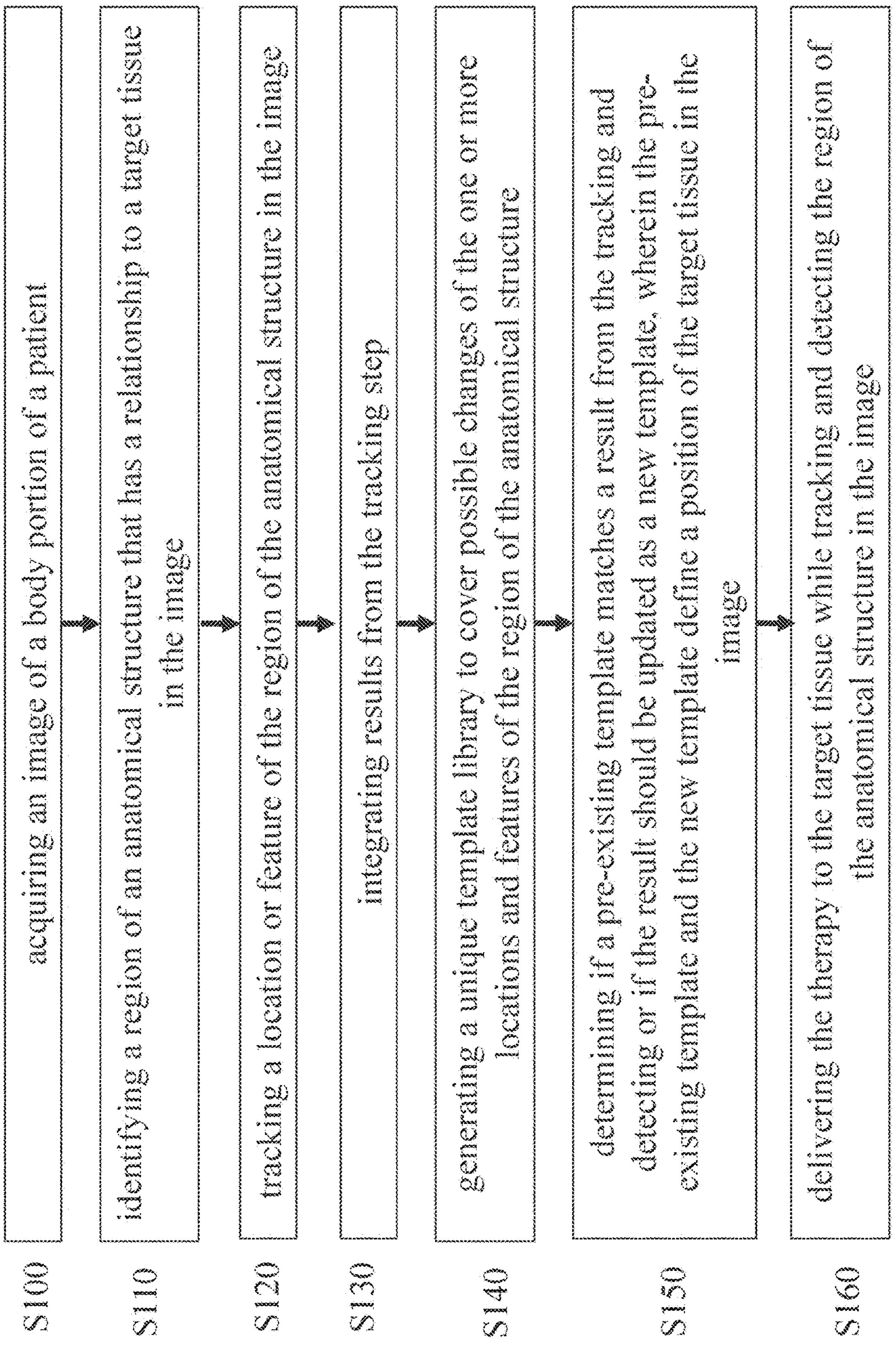
FIG. 13 illustrates a method of tracking a target tissue and delivering therapy to a target tissue, in accordance with a preferred embodiment.

FIG. 13 illustrates a method of tracking a target tissue and delivering therapy to a target tissue, in accordance with a preferred embodiment. As shown in FIG. 13, a method for imaging during delivery of a therapy of a preferred embodiment includes the steps of acquiring an image of a body portion of a patient S100; identifying a region of an anatomical structure that has a relationship to a target tissue in the image S110; tracking a location or feature of the region of the anatomical structure in the image S120; integrating the results from the tracking S130; generating a unique template library to cover possible changes of the one or more locations and features of the region of the anatomical structure S140; determining if a pre-existing template matches a result from the tracking or if the result should be updated as a new template, wherein the pre-existing template and the new template define a position of the target tissue in the image S150; and delivering the therapy to the target tissue while tracking the region of the anatomical structure in the image S160. In some embodiments, the method preferably functions to track a region of an anatomical structure, such that the position of the anatomical structure correlates with a position of a target tissue. The method may be used for delivering ultrasound to denervate a renal artery but, additionally or alternatively, can be used for any suitable applications, clinical or otherwise. For example, the method may be used to deliver ultrasound to a kidney, gallbladder, bile duct, or ureter to disrupt kidney, gallstones, bile duct stones, or ureter stones, respectively.

As shown in FIG. 13, step S100 includes acquiring an image of a body portion of a patient. Step S100 preferably functions to image a region of an anatomical structure of a patient, such that a location and/or feature of a region of the anatomical structure may correspond to a position of the target tissue for receiving therapy. As described above, the image may be acquired in B-mode, Harmonic image, color Doppler, color power Doppler, or directional color power Doppler mode image. In some embodiments, the imaging may be performed using ultrasound or any other type of imaging modality, optical or otherwise.

As shown in FIG. 13, step S110 includes identifying a region of an anatomical structure that has a relationship to a target tissue in the image. Step S110 preferably functions to identify a region of an anatomical structure that moves, deforms, or otherwise tracks in a similar manner as the target tissue, such that the anatomical structure may be tracked while the target tissue is receiving therapy. For example, if the target tissue moves 2 cm to the right in the image, the region of the anatomical structure being tracked should also move 2 cm to the right. In some embodiments, the target tissue is the anatomical structure being tracked.

As shown in FIG. 13, step S120 includes tracking a location or feature of the region of the anatomical structure in the image. Step S120 preferably functions to track a location or feature of a region of the anatomical structure using a tracker and detector, such that the therapy module may be notified of a change in location or feature of the target tissue. In some embodiments, step S120 occurs in response to a change in location or feature of the region of the anatomical structure.

As shown in FIG. 13, step S130 includes integrating the results from the tracking with the tracker and detector. Step S130 preferably functions to determine if the results from the tracker and detector will be used and if a new template should be generated based on the results from the tracker and detector. For example, if the tracking results from the tracker and detector, respectively, match a key template, as described above, the integrator will use the detector results and instruct the therapy module to deliver therapy to the target tissue, such that a position of the target tissue is known by the integrator and transmitted to the therapy module.

As shown in FIG. 13, step S140 includes generating a unique template library to cover possible changes of the one or more locations and features of the region of the anatomical structure. Step S140 preferably functions to maintain a template pool of possible locations and/or features of the anatomical structure being tracked by the imaging module, such that the template pool was generated over time from previous images. Each result from the tracker and detector may be compared to the template pool to determine if 1) the result matches a template and thus the template can inform the therapy module as to the position of the target tissue or 2) the result does not match a template and a new template needs to be generated and thus the new template can inform the therapy module as to the position of the target tissue, as further recited in S150. As shown in FIG. 13, step S160 includes delivering the therapy to the target tissue while tracking the region of the anatomical structure in the image. Step S160 preferably functions to deliver therapy to the target tissue while consistently aligning an orientation, position, or otherwise direction of the therapy module with the target tissue. The therapy module, as described herein, receives information from the imaging module that pertains to a position of the target tissue, such that the tracker and detector track a position of the target tissue by tracking a region of an anatomical structure.

In some embodiments, the method of FIG. 13 further includes substantially continuously delivering therapy to the target tissue despite a change in one or more locations and features of the region of the anatomical structure. The therapy module may continue delivering therapy despite a change since the imaging module may alert, notify, or otherwise inform the therapy module of the change, and the therapy module may adjust accordingly.

In some embodiments, the method of FIG. 13 further includes stopping the imaging of the region of the anatomical structure when the region of the anatomical structure is undetectable. For example, the anatomical structure may move perpendicularly away from the imaging plane, such that the region of the anatomical structure is undetectable. In some embodiments, the imaging module may automatically recover (e.g. without user intervention) the region of the anatomical structure location or feature, such that therapy delivery may resume.

Further, automatically recovering the region of the anatomical structure location or feature may occur by first determining a last known location or feature of the region of the anatomical structure in the image (logic function). In some embodiments, the last known location or feature may correspond to a template from the template pool.

In some embodiments, the method of FIG. 13 further includes filtering the image, such that the anatomical structure can be tracked in the filtered image. The image may be filtered using a moving average filter or any other type of filter.

In some embodiments, the method of FIG. 13 further includes generating a new template when the pre-existing template does not match the tracking results, such that the new template corresponds to a position of the target tissue in the image. In some embodiments, the new template is assigned as the key template, as described above. In some embodiments, the new template may be generated by the integrator.

In some embodiments, the method of FIG. 13 is implemented in a graphics processing unit (GPU), FPGA, and/or DSP to further reduce the computation time of the tracker, detector and integrator.

As described herein, a method for treatment includes: acquiring with an imaging module an image of a body portion of a patient; identifying a region of an anatomical structure that has a relationship to a target tissue in the image; tracking a location and/or a feature of the region of the anatomical structure in the image; transforming a target position of the target tissue from an imaging space associated with the imaging module to a treatment space associated with a therapy module through one or more position sensors and a transmitter; and delivering a therapy with the therapy module to the target tissue while tracking the region of the anatomical structure. In some embodiments, the act of transforming is performed to bring a target position of the target tissue (e.g., renal artery) in the imaging space (e.g., ultrasound imaging coordinate) to a transformed target position in the treatment space (e.g., therapeutic array coordinate).

Various techniques maybe employed to achieve such objective. For example, in some cases, a real-time electromagnetic tracking system with sub-millimeter and sub-degree accuracy may be used. The magnetic field sensor may be attached on the handle of the imaging transducer, and a magnetic field transmitter may be attached to the base of therapeutic treatment module. The magnetic field transmitter generates a magnetic field. When the magnetic sensor is placed inside controlled, varying magnetic fields generated from the transmitter, voltage are induced in the sensor coils. These induced voltages can be used by the measurement system to calculate the position and the orientation of the magnetic field sensor in 3D space. In such cases, after the renal artery target position is detected by ultrasound imaging (in image coordinate), the transformation of the position may be performed as follows: 1) the treatment position and orientation of a target in the image coordinate are linked with the magnetic field sensor position and orientation based on mechanical design and calibration (in magnetic sensor coordinate); 2) the target position and orientation in the magnetic sensor coordinate are then transformed into the treatment module coordinate by the detection of the sensor position and orientation in the magnetic field generated by the magnetic field transmitter, and 3) the target position and orientation in the treatment module coordinate are further transformed into the coordinate of the therapeutic array. In some cases, the third transformation above is not needed if the coordinate frame of the therapeutic array is aligned with the treatment module coordinate frame. Therefore, knowing the position and orientation of the imaged target relative to the coordinate frame of the therapeutic array through the above transformations, the therapeutic system can adjust the mechanical movement of the therapeutic array and/or the phases of the array elements to deliver the ultrasound energy at the imaged treatment target.

In other embodiments, non-magnetic position measurement system may be used. This has the advantage of eliminating the possibilities of wrong targeting when a metal object gets close to the magnetic sensor and the transmitter. For example, in other embodiments, optical position measurement system may be used that measures the 3D positions of either active or passive markers affixed to application-specific tools. In one implementation, three different optical tool plates with at least three optical markers on each plate may be provided. One plate with optical markers is attached with the handle of the imaging transducer. The other two plates are attached on the left and right sides of the therapeutic treatment module separately. An optical position sensor system may be attached to the base of therapeutic treatment module. The optical position sensor system emits infrared (IR) light from its illuminators, similar to the flash on a conventional camera. The emitted IR light reflects back to the Position Sensor off markers (which may be spherical or semi-spherical) on the passive tool plates. The optical position sensor system then measures the positions of the markers and calculates the positions and orientations of the tool plates. The relationship of both positions and orientations between the tool plate attached to the imaging transducer (e.g., the handle) and the treatment module can be determined by the position sensor system at a rate of 20 Hz in real-time. To further optimize the detection accuracy of the positions and orientations between the imaging transducer and treatment module, the two plates which are attached along the left and right side of the treatment module are orientated to the optimized angles for treating the right and left renal denervation separately. In such cases, after the renal artery target position is detected by ultrasound imaging (in image coordinate), the transformation of the positions and orientations of the treatment target from the imaging coordinate to the therapy coordinate may be performed as follows: 1) the target position and orientation in the image coordinate are linked with the optical plate position (of the imaging transducer) based on mechanical design and calibration (to obtain treatment position and orientation in imaging tool plate coordinate); 2) the target position and orientation in the imaging tool plate coordinate are further transformed into optical position sensor coordinate frame; 3) the target position and orientation in the position sensor coordinate frame are then transformed into either left or right tool plate coordinate frame attached on the treatment module depending on the treatment of right or left side renal nerves; 4) the target position and orientation in the left/right treatment tool plate coordinate frame are further transformed to the therapeutic array coordinate frame based on mechanical design dimension and calibrations. Thus, the therapeutic system may control the therapeutic array to deliver the ultrasound energy to the treatment target through the above transformations by adjusting the mechanical movement of the therapeutic array and/or electronic phasing steering (e.g., in depth direction, and/or other direction(s)).

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the imaging module and/or the therapy module. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, for example Versatile Data Acquisition System (VDAS), but any suitable dedicated hardware or hardware/firmware combination can alternatively or additionally execute the instructions.

In other embodiments, instead of or in addition to using histogram(s), a feature matching technique such as Normalized Cross Correlation method, Sum Square Difference method, Sum Absolute Difference method, etc., may be used.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating target tissue associated with a renal artery of a patient, the renal artery moving during the treating due to breathing and blood flow of the patient, comprising:

identifying the renal artery and the target tissue;

applying therapeutic energy to the target tissue;

tracking a location of the renal artery and a location and a feature of the target tissue during said applying;

adjusting said applying based on said tracking to apply therapeutic energy to the tracked location of the target tissue;

generating a template library comprising a plurality of templates identifying at least one of a prior location and a prior feature of the target tissue for a respective one of several previous target positions;

predicting a future position of the target tissue by comparing current tracking results, the current tracking results comprising a current location and a current feature of the target tissue, with each of a plurality of templates in the template library corresponding to the several previous target positions, determining a respective degree of mismatch between the current tracking results and each of the plurality of templates, identifying a matched template having a lowest mismatch value, determining whether the lowest mismatch value is within a threshold value, in response to determining that the lowest mismatch value is within the threshold value, obtaining, from the matched template, a prior location of the target tissue and a prior feature of the target tissue associated with a prior target position, and determining the future position using a weighted function based on the several previous target positions and the prior location obtained from the matched template;

applying therapeutic energy to the predicted future position; and in response to the target tissue becoming undetectable during said tracking, automatically re-detecting the target tissue without user intervention when the target tissue becomes detectable.

2. The method of claim 1, wherein said tracking further comprises tracking blood flow through the renal artery during said applying.

3. The method of claim 1, further comprising catheterizing the patient with a catheter, and wherein said applying therapeutic energy is performed with said catheter, wherein the target tissue is a renal nerve.

4. The method of claim 1, wherein the therapeutic energy is ultrasound energy.

5. The method of claim 1, wherein said identifying and said tracking are performed by ultrasound imaging.

6. The method of claim 1, wherein said applying, said tracking, and said adjusting are repeated to form a plurality of lesions in the target tissue.

7. The method of claim 6, wherein:

said applying forms a plurality of lesions associated with the renal artery, and each lesion is spaced 5 mm or less from each adjacent lesion.

8. The method of claim 6, wherein:

said applying forms a plurality of lesions associated with the renal artery, and each lesion is spaced 1 mm or less from each adjacent lesion.

9. The method of claim 6, wherein:

said applying forms a plurality of lesions associated with the renal artery, and said identifying the renal artery and the target tissue comprises identifying the renal artery and the target tissue in less than 1 second.

10. The method of claim 1, wherein said identifying further comprises imaging the target tissue with a two-dimensional array configured to acquire 3D ultrasound images inside the body of the patient; and wherein said tracking further comprises utilizing said imaging to obtain a position the current location and the current feature of the target tissue during the period of time of said applying.

11. The method of claim 1, wherein the current feature of the target tissue and the prior feature of the target tissue each comprise at least one of intensity, density, contrast, and shape.

12. The method of claim 11, wherein each of the plurality of templates comprises a feature histogram of a previous location or a previous feature of the target tissue.

13. The method of claim 12, wherein determining the respective degree of mismatch comprises determining a distance between a feature histogram of the current location or the current feature of the target tissue and the feature histogram of each of the plurality of templates.

14. The method of claim 13, wherein determining the future position of the target tissue using the weighted function comprises:

assigning respective weights to the several previous target positions and to the prior location obtained from the matched template; and determining the future position of the target tissue based on the weighted function of the several previous target positions and the prior location obtained from the matched template.

15. The method of claim 14, further comprising:

in response to determining during said tracking that the target tissue is undetectable, continuing to acquire tracking data; and automatically re-detecting the target tissue without user intervention by comparing the tracking data acquired after the target tissue becomes undetectable with the plurality of templates in the template library until the matched template having the lowest mismatch value within the threshold value is identified.

16. A method of treating a renal artery of a patient, where the renal artery moves during treatment due to respiration and blood flow pulsatility of the patient, comprising identifying the renal artery;

applying therapeutic energy to the renal artery;

monitoring a location and a feature of the renal artery during said applying to generate feedback;

utilizing said feedback to adjust said applying;

generating a template library comprising a plurality of templates, each template identifying at least one of a prior location and a prior feature of the renal artery for a respective one of several previous renal artery positions;

predicting a future position of the renal artery by comparing current monitoring results, the current monitoring results comprising a current location and a current feature of the renal artery, with each of a plurality of templates in the template library corresponding to the several previous renal artery positions, determining a respective degree of mismatch between the current monitoring results and each of the plurality of templates, identifying a matched template having a lowest mismatch value, determining whether the lowest mismatch value is within a threshold value, in response to determining that the lowest mismatch value is within the threshold value, obtaining, from the matched template, a prior location of the renal artery and a prior feature of the renal artery associated with a prior renal artery position, and determining the future position using a weighted function based on the several previous renal artery positions and the prior location obtained from the matched template;

applying therapeutic energy to the predicted future position; and in response to the renal artery becoming undetectable during said monitoring, automatically re-detecting the renal artery without user intervention when the renal artery becomes detectable.

17. The method of claim 16, wherein said utilizing comprises utilizing said feedback to adjust at least one of a location and an output of said applying therapeutic energy.

18. The method of claim 16, wherein the therapeutic energy is ultrasound energy.

19. The method of claim 16, wherein:

said applying forms a plurality of lesions associated with the renal artery, and each lesion is spaced 5 mm or less from each adjacent lesion.

20. The method of claim 16, wherein:

said applying forms a plurality of lesions associated with the renal artery, and each lesion is spaced 1 mm or less from each adjacent lesion.

21. A method of treating an anatomical structure associated with a renal artery of a patient, the renal artery moving during the treating due to breathing and blood flow of the patient, comprising:

imaging the anatomical structure associated with the renal artery in three dimensions;

applying therapeutic energy to the anatomical structure associated with the renal artery;

continuing said imaging the anatomical structure during said applying to obtain a current location and a current feature of the anatomical structure;

adjusting said applying based on said continuing imaging;

generating a template library comprising a plurality of templates, each template identifying at least one of a prior location and a prior feature of the anatomical structure for a respective one of several previous positions of the anatomical structure;

predicting a future position of the anatomical structure by comparing current imaging results, the current imaging results comprising the current location and the current feature of the anatomical structure, with each of a plurality of templates in the template library corresponding to the several previous positions of the anatomical structure, determining a respective degree of mismatch between the current imaging results and each of the plurality of templates, identifying a matched template having a lowest mismatch value, determining whether the lowest mismatch value is within a threshold value, in response to determining that the lowest mismatch value is within the threshold value, obtaining, from the matched template, a prior location of the anatomical structure and a prior feature of the anatomical structure associated with a prior position of the anatomical structure, and determining the future position using a weighted function based on the several previous positions of the anatomical structure and the prior location obtained from the matched template;

applying therapeutic energy to the predicted future position; and in response to the anatomical structure becoming undetectable during said continuing imaging, automatically re-detecting the anatomical structure without user intervention when the anatomical structure becomes detectable.

22. The method of claim 21, wherein said imaging is performed by a two-dimensional array that acquires three-dimensional images of the anatomical structure.

* * * * *